US010952664B2

(12) United States Patent
Bergqwist et al.

(10) Patent No.: US 10,952,664 B2
(45) Date of Patent: Mar. 23, 2021

(54) MOBILE APPARATUS, METHOD AND SYSTEM FOR PROCESSING BLOOD SUGAR AFFECTING FACTORS

(75) Inventors: Thomas Bergqwist, Staffanstorp (SE); George Sioustis, Löddeköpinge (SE)

(73) Assignee: Cross Technology Solutions AB, Lund (SE)

( * ) Notice: Subject to any disclaimer, the term of this patent is extended or adjusted under 35 U.S.C. 154(b) by 853 days.

(21) Appl. No.: 12/307,908

(22) PCT Filed: Jul. 19, 2007

(86) PCT No.: PCT/EP2007/057495
§ 371 (c)(1),
(2), (4) Date: Aug. 25, 2009

(87) PCT Pub. No.: WO2008/009737
PCT Pub. Date: Jan. 24, 2008

(65) Prior Publication Data
US 2010/0047745 A1   Feb. 25, 2010

(30) Foreign Application Priority Data

Jul. 19, 2006  (SE) .................... 0601580-4

(51) Int. Cl.
| G16H 20/60 | (2018.01) |
| A61B 5/00 | (2006.01) |
| A61B 5/145 | (2006.01) |
| G16H 20/17 | (2018.01) |
| A61B 5/22 | (2006.01) |
| G16H 40/67 | (2018.01) |

(52) U.S. Cl.
CPC .......... *A61B 5/411* (2013.01); *A61B 5/14532* (2013.01); *A61B 5/14546* (2013.01); *G16H 20/17* (2018.01); *G16H 20/60* (2018.01); *A61B 5/221* (2013.01); *A61B 5/7465* (2013.01); *G16H 40/67* (2018.01)

(58) Field of Classification Search
CPC ........ G06Q 50/22; G06Q 50/24; A61B 5/411; A61B 5/14532; A61B 5/14546; A61B 5/7465; A61B 5/221; G06F 19/3456; G06F 19/3475; G06F 19/3418
USPC ....................................... 434/127
See application file for complete search history.

(56) References Cited

U.S. PATENT DOCUMENTS

| 6,478,736 B1 | 11/2002 | Mault | |
| 7,041,468 B2 * | 5/2006 | Drucker et al. | ................ 435/14 |

(Continued)

FOREIGN PATENT DOCUMENTS

EP            1 622 059 A1    2/2006

*Primary Examiner* — Robert P Bullington
(74) *Attorney, Agent, or Firm* — Inskeep IP Group, Inc.

(57) ABSTRACT

A mobile apparatus is adapted to be handheld and configured for electronic processing of blood sugar affecting factors includes a first central processing unit arranged for processing of patient critical information objects, at least one memory comprising a plurality of in advance stored food units and values of at least one related blood sugar affecting parameter, an input unit arranged to provide user input such as a choice of food units and an amount thereof, a display arranged for visualization of food units for said user input, and for visualization of summed up blood sugar affecting parameters, and a second central processing unit arranged for processing of patient non-critical information objects.

37 Claims, 23 Drawing Sheets

(56) References Cited

U.S. PATENT DOCUMENTS

| | | | |
|---|---|---|---|
| 7,624,028 B1* | 11/2009 | Brown | 705/3 |
| 7,761,312 B2* | 7/2010 | Brown | 705/3 |
| 7,998,069 B2* | 8/2011 | Zivitz | G06F 19/3456 600/300 |
| 8,165,893 B1* | 4/2012 | Goldberg et al. | 705/2 |
| 8,326,546 B2* | 12/2012 | Stewart | G06F 19/3456 600/365 |
| 8,328,719 B2* | 12/2012 | Young | G01N 33/48785 422/400 |
| 8,348,843 B2* | 1/2013 | Young | G01N 33/48785 422/400 |
| 8,551,039 B2* | 10/2013 | Veit | A61B 5/14532 600/316 |
| 8,974,387 B2* | 3/2015 | Shadforth | A61B 5/14532 600/300 |
| 9,008,803 B2* | 4/2015 | Blomquist | G06F 19/3406 604/151 |
| 9,504,412 B2* | 11/2016 | Schaible | G06F 19/345 |
| 9,563,743 B2* | 2/2017 | Strachan | A61B 5/14532 |
| 9,693,734 B2* | 7/2017 | Horseman | G06F 19/3418 |
| 9,710,788 B2* | 7/2017 | Horseman | G06Q 10/105 |
| 2001/0056359 A1* | 12/2001 | Abreu | 705/3 |
| 2003/0032867 A1 | 2/2003 | Crothall et al. | |
| 2003/0076983 A1 | 4/2003 | Cox | |
| 2003/0204412 A1 | 10/2003 | Brier | |
| 2003/0212579 A1* | 11/2003 | Brown | A61B 5/411 705/2 |
| 2004/0180810 A1* | 9/2004 | Pilarski | G06F 19/3456 600/300 |
| 2005/0010442 A1* | 1/2005 | Kragh | 705/2 |
| 2005/0266385 A1 | 12/2005 | Bisogno | |
| 2007/0016449 A1* | 1/2007 | Cohen | G06F 19/3406 705/3 |

\* cited by examiner

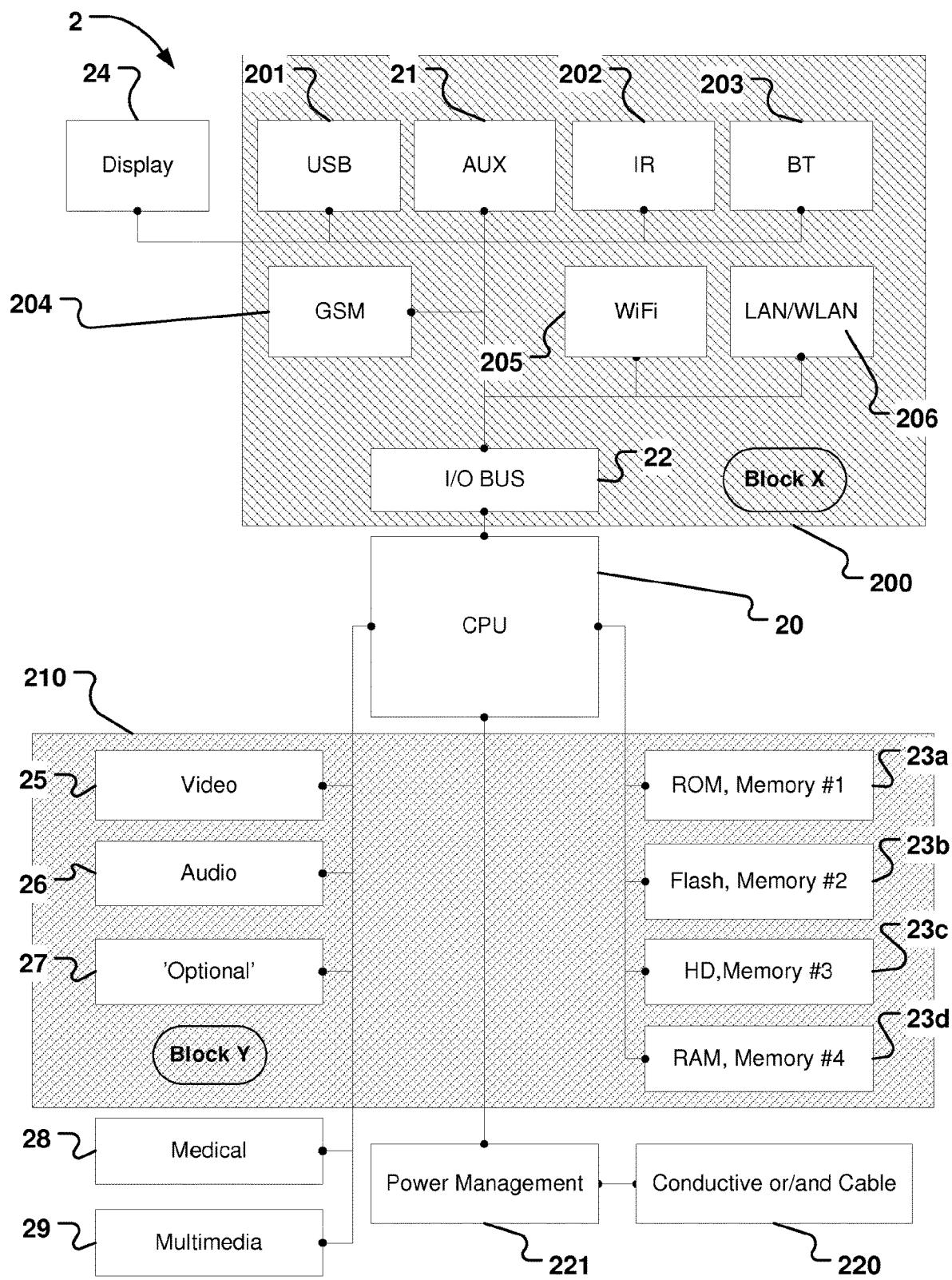
Fig. 2A    Singel processor, full functionality

Double processor, split functionality

Double processor, Mirror functionality (* Kh = net carbohydrates or carbohydrates )

(* valid also for diabetic related medicines)

MOBILE APPARATUS, METHOD AND SYSTEM FOR PROCESSING BLOOD SUGAR AFFECTING FACTORS

RELATED APPLICATIONS

This application claims priority to International Patent Application No. PCT/EP2007/057495, International Filing Date 19 Jul. 2007, entitled Mobile Apparatus, Method And System For Processing Blood Sugar Affecting Factors, and to Swedish Application No. 0601580-4 filed 19 Jul. 2006 entitled Anordning Och Metod För Sammanställning Av Blodsockerpåverkande Faktorer, both of which are hereby incorporated by reference.

FIELD OF THE INVENTION

This invention pertains in general to the field of processing of blood sugar affecting factors. More particularly the invention relates to an apparatus and method for processing of blood sugar affecting factors.

BACKGROUND OF THE INVENTION

Characterizing blood glucose or blood sugar response in an individual is an issue in many areas of human life. For instance in the treatment of diabetes, in order to estimate an amount of insulin required by a diabetic person to normalize the blood sugar level, is critical to maintaining health.

World Health Organization (WHO) has categorized the rapid increase of diagnosed diabetics in the world as epidemic. The alarming trend increases the costs of diabetes (a medical state with costly known health care side effects for the society and the affected individuals). This is a significant health care burden in the world that increases every day. WHO estimates the number of diagnosed diabetics to reach 300 millions by the year 2025 (the diabetes industry estimates that there is one undiagnosed diabetic on every diagnosed diabetic, the number in risk zone of developing diabetes over time increases with a factor×3 du to i.e. over weight and food habits etc). With the apparatus diabetics can be guided and fine tune their lifestyle end her by decrease their need for insulin with ~30% and some individuals can completely end their medication (proven by studies in Sweden).

The intake of food influences the blood sugar level. Foodstuff is characterized, among other things, in terms of the carbohydrate content or the Glycemic Index (GI) thereof. Attempts have been made to relate the level of blood sugar to the food intake calculated in GI. However, this method is highly inaccurate. Furthermore, the intake of food is only one of many parameters that influence the blood sugar level.

According to the prior art, various types of systems are known for monitoring food intake for an individual.

Such a system is disclosed in US2005/0266385. US2005/0266385A1 discloses a computer program, method, and system for monitoring nutrition content of consumables and for facilitating menu planning. A hand-held apparatus for providing nutrition content information is disclosed, which comprises a computer-readable memory within housing to allow a user to monitor, tailor, plan or review their intake in light of a health-related interest or concern, such as, for example, weight-loss, food allergies, or diabetes or other nutrition affected illnesses or disabilities. Consumables are categorized and displayed in lists associated with an appropriate color to draw attention to relative nutrition content and to facilitate quicker and easier evaluation of a consumable of interest. Summaries are provided of a user's actual intake in light of a pre-established target intake for a particular day. Detailed reports may be generated showing consumption over a user-specifiable time period.

A problem with this type of previously known systems for monitoring and compiling food based nutrition intake for an individual, is that it lacks the ability to, in a precise manner, provide glycemical indexes and other blood sugar affecting factors in combination. Furthermore, the systems lack the possibility to, in an uncomplicated manner, compile and analyze glycemical indexes and others blood sugar affecting factors. However, these factors are not sufficient for a reliable analysis of the status of a patient.

In WO06079124A2 an insulation bolus dosage calculating device. Insulin boluses for Type 1 diabetics are calculated to improve their blood glucose control. An algorithm is implemented as either a portable electronic device (PED) or a slide rule device. Further operation of an insulin dosage calculation device is controlled.

A system for assisting a person to maintain blood glucose level between predetermined limits is disclosed in WO0205702A2. The system comprises an electronic device that has a display, a clock, a memory, and a processor; and a software program executable by the processor of the electronic device. The electronic device receives nutritional data of food consumed by the person, for calculating a blood glucose level for the person using the nutritional data and a glycemic response model for the person. The blood glucose level is presented to the person on the display of the electronic device.

A disadvantage with this type of systems for monitoring and compiling food nutrition intake for an individual is that they are restricted to specific areas of usage, e.g. weight loss or control of insulin bolus of a diabetic. With this respect, an undesired inclination of the food based compilation towards such an area of usage results.

An issue with this type of known systems is that they give an unsatisfactory monitoring and lack analysis of for example a diabetic's health condition. A disadvantage with such systems for monitoring and compiling only food nutrition intake is the risk of not noticing conditions with increased risk for hyperglycemia and hypoglycemia.

A system and method for registering, predicting and/or preventing inadvertent conditions of hyperglycemia and hypoglycemia, would be advantageous for preventing potentially dire consequences.

Further, the systems and methods known in the prior art are rather complicated and not user friendly and flexible in every day life. Furthermore, reliability of the systems has potential for improvement, as well as patient safety thereof.

Hence, there exists a need to process, visualize, calculate and to put together blood sugar affecting parameters, e.g. for a plural of ingested or select food units since food units properties in cooperation influences the result or the over all blood sugar level.

Therefore, an improved device and method for processing blood sugar affecting factors would be advantageous and in particular allowing for increased flexibility, reliability, patient safety, and/or cost-effectiveness would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device, a system comprising a plurality of such devices, a method, a computer program, and a workstation, according to the appended patent claims.

According to one aspect of the invention, a method is provided, for summarization of glycemical load on the human body.

According to another aspect of the invention, a lifestyle profile is provided by the functionality for analysis, by the HW and SW configuration of the apparatus.

According to yet another aspect of the invention, an apparatus for interactive communication is provided. The apparatus is adapted to support an individuals medical condition and to be integrated in a system enabling monitoring of a multitude of users/patients.

The apparatus may be a mobile, portable apparatus adapted to be handheld and configured for electronic processing of blood sugar affecting factors. The apparatus comprises a first central processing unit arranged for processing of patient critical information objects, at least one memory comprising a plurality of in advance stored food units and values of at least one related blood sugar affecting parameter, such as glycemic indexes and/or glycemical loads and/or carbohydrate contents and/or PH value for respective food unit, an input unit arranged to provide user input for at least one of said food units, such as a choice of one of said food units and an amount thereof, a display arranged for visualization of at least one of said food units for said user input, and for visualization of summed up blood sugar affecting parameters, and a second central processing unit arranged for processing of patient non-critical information objects, such as multimedia objects to be visualized on said display.

According to another aspect of the invention, a use of such an apparatus is provided for calculation of glycemical indexes, glycemical load and net carbohydrate for selected food units.

According to yet another aspect of the invention, a graphical man machine interface of an apparatus according to the above aspect is provided. The graphical interface comprises visualization of a blood sugar indicative curve in said apparatus' display, in a variable time viewing scale; at least one indicator for a meal time relative said blood sugar indicative curve; and a range of normoglycemic blood sugar values that is visually indicated by a band along said blood sugar indicative curve and adjacent bands of hyperglycemic and hypoglycemic ranges.

According to another aspect of the invention, a system comprising a plurality of said apparatuses is provided. The system comprises a communication path from said apparatuses to a remote database; and a database to which said apparatuses are connectable for communicating stored data objects via said communication path, and a computing device remote to said apparatuses configured to screen data objects stored in said database to choose selected users of a population of users of said apparatuses.

According to a further aspect of the invention, a method of using the system according to the previous aspect is provided. The method comprises screening a population of users of said plurality of apparatuses for enabling a health provider to follow up said population of users.

According to a further aspect of the invention, A computer program for processing by a computer is provided. The computer program comprises code segments for performing the method according to the previous aspect. The computer program may be embodied on a computer-readable medium.

Further embodiments of the invention are defined in the dependent claims, wherein features for the second and subsequent aspects of the invention are as for the first aspect mutatis mutandis.

Some embodiments of the invention provide for increased operational safety of an apparatus.

Some embodiments of the invention provide for increased patient safety.

The invention relates to an apparatus and method for electronically compiling blood sugar affecting factors. More particularly the invention relates to an apparatus and method for compiling sensible blood sugar influencing factors for in a database of select food units on the basis of registered amounts of respective food unit intake.

This type of appliances and methods are for example suitable for persons that of health reasons try to monitor their food intake or their lifestyle, i.e. persons with diabetes. This type of apparatus and method may also be used of persons that desire to loose weight and of athletically minded persons in order to increase their performance capacity.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 2A is a schematic block diagram of a basic hardware setup of an apparatus according to an embodiment having a single processor;

DESCRIPTION OF EMBODIMENTS

Figure 1:
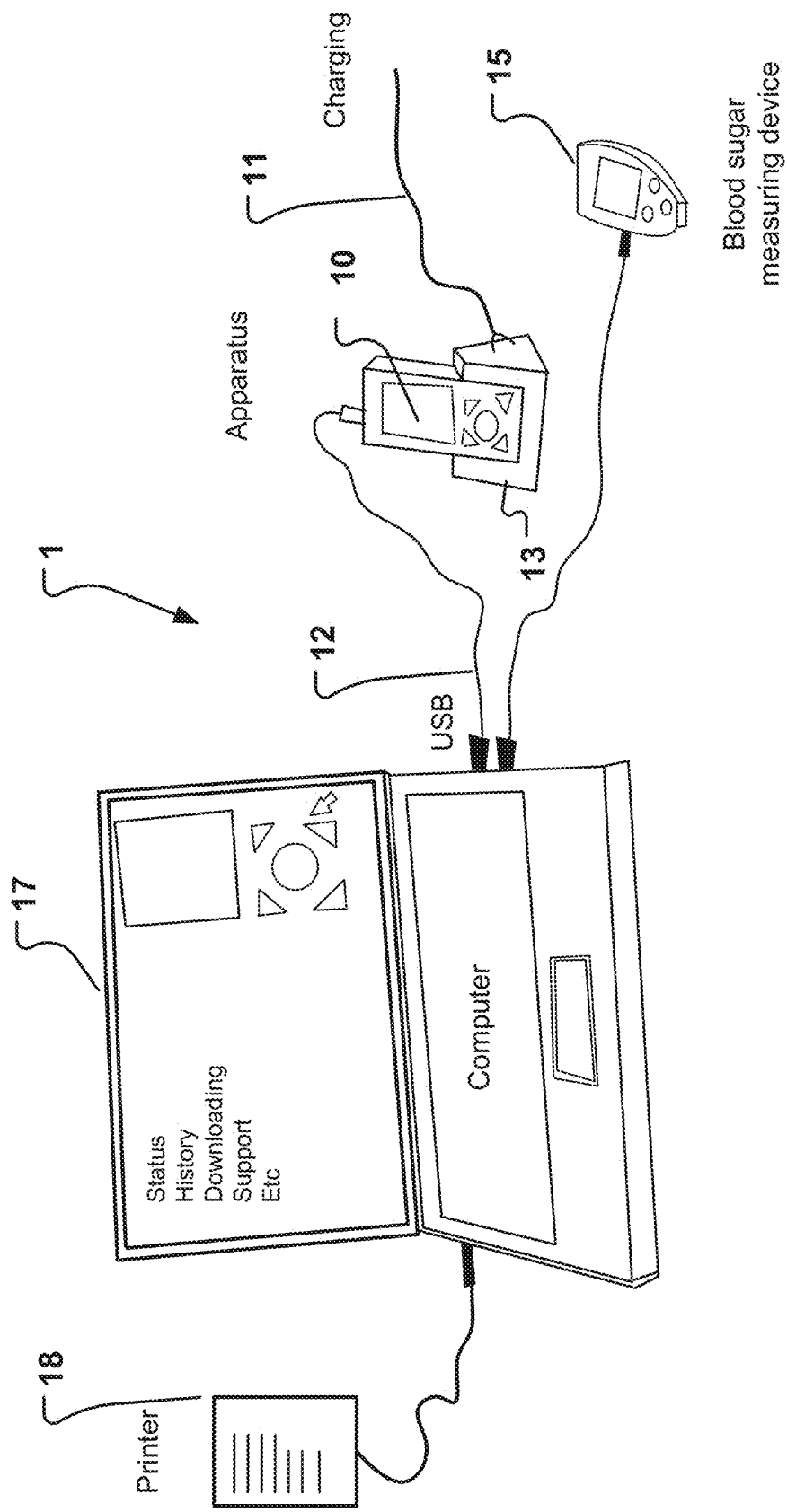
FIG. 1 is a schematic illustration of an apparatus of an embodiment connected to a base station.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a portable apparatus and in particular to a handheld portable apparatus. However, it will be appreciated that the invention is not limited to this application but may be applied to or implemented in many other forms, such as a software to be used with a mobile phone or a personal digital assistant (PDA). The apparatus may also be integrated with other medical technical equipments (medical devices), such as a blood sugar measurement device, a blood pressure monitor, a pedometer, a patient activity meter, etc.

Before discussion the technical features and effects of embodiments, some definitions will be given in order to facilitate understanding of the present specification.

Glycemic Index (GI)

The glycemic index (GI) is defined as the total surface under a curve that describes the blood sugar concentration within two hours after meal time, when one eats 50 grams available carbohydrates in food in relation to when one eats 50 grams available carbohydrates in a reference food, i.e. white bread or glucose.

In order to calculate the GI, the area is divided for the select food with the area for the reference, whereupon the quota is multiplied with 100. Glycemic Index GI is a relative value and has no unit.

It is important to note that the comparison concerns equal amount available carbohydrates, not equal amount of food in general.

Eatables with a high Glycemic Index GI may be called "fast foods" while foodstuffs with a low Glycemic Index GI may be called "slow foods". Thus, Glycemic Index GI is a way to classify how different foodstuffs influence the blood sugar value in the course of time.

Hence, the Glycemic Index GI is a complicated concept for the consumer to use in the correct way. Many factors, including for instance the raw food's properties (e.g. type, fiber content, ripeness, etc); the processing of the food (e.g. heat, fermentation, grinding, etc.); and which type of carbohydrates the product contains. All these various factors determine which effect the product will have on the blood sugar level of a person after a meal.

In order to exactly know what Glycemic Index GI a product has, this must be clinically tested with that product.

Table values can only be used as a coarse estimate.

A food's Glycemic Index GI is influenced by the amount of glycemical influencing parameters, such as, amongst other things, how fast the stomach is emptied, digestion and absorption of carbohydrates in the small intestine, type of monosaccharides and disaccharides, properties of starch that may occur, production and coking processes etc. For example has the type of starch (straight or branched) signification.

Branched starch (amylopectin) gives a somewhat higher Glycemic Index GI than straight starch (amylose).

Additional glycemical influencing parameters are the particles size and cell structure of the foodstuff.

Breads based on the whole grains have for example a lower Glycemic Index GI than breads of finely ground flours, irrespective of a fiber content.

Slow baking (during a long time) and sour dough fermentation lowers a bread's Glycemic Index GI. The amount of fibers may also lower the Glycemic Index GI for a product but it is required relatively large quantities of fibers in order to give that effect on the Glycemic Index GI of a foodstuff. Vinegar may contribute to a lower blood sugar after a meal.

The stomach's emptying speed may also be influenced by the amount of fat and protein in the diet. But also here large quantities are required in order to make a higher Glycemic Index GI food product to become a slower Glycemic Index GI food product.

Glycemic Load (GL)

Another concept that is more relevant to use is the glycemic load, GL (Glycemic Load, GL). Glycemic Load GL is equal to grams of carbohydrates in a normal portion× GI/100. This concept considers how large a normal portion is of various foodstuff, and how the blood sugar response will be influenced and affected.

This is therefore a way to compare the Glycemic Index GI in different foodstuffs with different carbohydrate contents. The Glycemic Index GI for potatoes is for instance higher than for pasta, while the Glycemic Load GL for potatoes is lower than that of pasta. This is due to the fact that a normal portion of potatoes contains a lower less amount of carbohydrates compared to a normal portion of pasta. This concept is therefore more relevant and practical to use.

Apparatus

The apparatus and method in accordance with the embodiments of the invention provide for blood sugar affecting factors to be processed in a precise manner, such as summarized, monitored and/or analyzed, in relation to the daily food intake and other blood sugar affecting parameters of a user of the apparatus or method.

This implies for instance that a diabetic person in a simple way is able to monitor his/her lifestyle in order to improve his/her health condition, monitor and to adapt, render more effective, or decrease his/her insulin dosage in a more precise manner in order to achieve normoglycemia, and to reduce the risk for resistance against insulin, as well as to reduce the risk for hypoglycemia or hyperglycemia. Thus, a diabetic person may in a simple way adopt his/her lifestyle in compliance with a recommended lifestyle, which may e.g. be drawn up by a medical professional. Furthermore, embodiments of the invention may provide for persons in physical training to monitor their lifestyle, in order to monitor or increase their performance capacity. Furthermore, embodiments of the invention may provide persons the opportunity to monitor their lifestyle, e.g. in order to achieve weight reduction. Achievement of weight reduction is a secondary effect of using the apparatus or method of embodiments. Weight reduction may comprise a loosing of weight of totally healthy users for aesthetic or cosmetic reasons.

Some embodiments of the apparatus or method may comprise a function for electronically summing-up blood sugar affecting factors.

The product apparatus, also called G-Pilot, is a hand held device that makes life easier for the user thereof, e.g., diabetics by being an information object communicator and carrier of how the "users" lifestyle affects and relates to the blood sugar level and insulin dozes.

The apparatus creates a personal Lifestyle profile based on the interrelationship between blood sugar affecting parameters such as; Specified food intake, activities, health conditions and actual blood sugar level and insulin dozes (medicine).

From this information the apparatus creates a concurrent blood sugar indication curve, giving the user the ability to plan the blood sugar level in relation to what the user plans to actually eat (before the food is eaten).

The function also helps a diabetic person to plan the insulin dozes before the meal and to follow up the actual effect on a specific meal combination.

The apparatus also gives information on what was the reason behind a specific blood sugar curve peak in the retrospective history (the Lifestyle Profile History); this e.g. simply by pointing on a curve peak, on a touch screen of the apparatus, e.g. with a finger. An information box will be shown with specified information on the meals/foods combined glycemical load (GL) and other historical blood sugar affecting and related parameters for that specific peak. This is described in more detail below with reference to FIG. 8.

This unique function enables for the user to learn and make conclusions to continuously improve and have control over the blood sugar level and his/her unique Lifestyle Profile.

The Lifestyle Profile history (per day, week, month ore more) may be transferred from the apparatus to a medical professional for follow up and decisions related to the treatment.

The apparatus described herein, the G-Pilot, creates a basic condition for the health provider to concentrate health care recourses to the most needing patients, by enabling follow up of patient populations (multitude of patients).

The apparatus described herein also helps to reduce the need for blood sugar regulating medicine (i.e. insulin) by 30% and/or the need can completely disappear (especial in early stages of T2 diabetes), creating direct health care cost reductions and patient life quality increasement.

FIG. 1 is a schematic illustration of a part of a system 1 comprising an apparatus 10 of an embodiment connected to a base station 17. The apparatus 10 is shown positioned in a docking station 13. The system 1 may further comprise remote computers connectable to a plurality of apparatuses 10, having a central database e.g. enabling screening of patient populations. These aspects of the system 1 will be described further below.

The docking station 13, shown in FIG. 1, comprises a charging and power supply main connection for charging a battery of the apparatus 10, and an interface, such as a USB connection 12, to an external device i.e. the computer base station 17.

A blood sugar measuring device 15 may optionally be connected to the base station 17 for providing blood sugar measurements. The blood sugar measuring device 15 may also be directly connected to the apparatus 10. The blood sugar measuring device 15 may also be integrated with apparatus 10.

Apparatus 10 may comprise or be connected to a barcode reader for input of data, e.g. from a food packaging identifying a specific food product and its related blood sugar affecting parameters.

In addition, or alternatively, the apparatus 10 may comprise a digital camera providing digital images for processing and analysis. By means of the digital camera, images of food to be eaten by the user of apparatus 10 may be entered into the apparatus for processing. Based on the image of the food, its blood sugar affecting parameters may be identified and transferred to the users lifestyle database.

In addition, or alternatively, the apparatus 10 may be connected to or integrated with other equipment, such as blood pressure monitors, blood sugar sensors, patient activity meters such as pedometers, pulsemeters or pacemakers having such a functionality. Patient activity meters are useful for estimating the patients blood sugar level as physical activity consumes energy, and thus the blood sugar level decreases faster with different types of physical activity.

Connections and interfaces of devices and apparatuses described herein may also be made wirelessly, e.g. via a mobile telephone, Bluetooth, a wireless LAN, etc.

The base station 17 provides communication with the apparatus 10, for instance it enables external uploading of information from the apparatus 10 or enables upgrading of information and software downloads of the apparatus 10. Furthermore, base station 17 provides printouts 18 and further communication, e.g. to an external database, e.g. via a peer to peer network, such as internet.

Figure 2B:
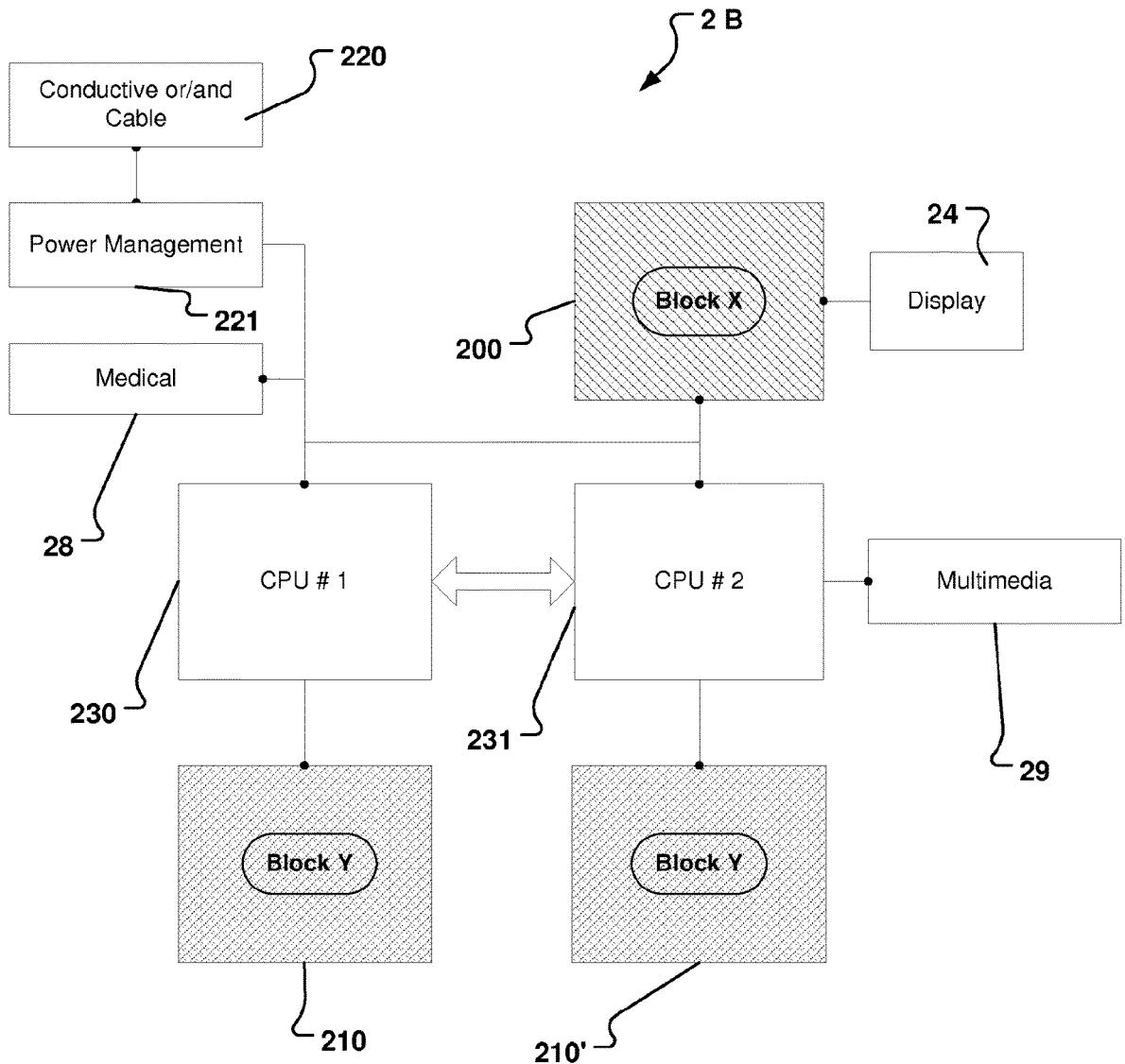
FIG. 2B is a schematic block diagram of a basic hardware setup of an apparatus according to an embodiment having double processors with split functionality.

FIG. 2 is a schematic block diagram of an embodiment of a basic hardware setup of an apparatus 10 having a single processor.

This schematic drawing shows an electronic device 2 comprising one central processing unit (CPU) 20.

A communication unit 200 comprises hardware components for communication purposes. The communication unite 200 comprises an I/O Bus 22 (Input/Output controller Bus), which communicates with units handling a display 24, a USB interface 201, an infrared interface 202, a Bluetooth interface 203, a GSM unit 204, or other high speed wireless radio transfer of data over the telecom network, AUX 21, WLAN/WiFi 206, and optional devices.

The CPU 20 communicates with Audio 26, video 25, multimedia 29 units in order to process data for different services/processes.

The CPU 20 communicates with a power management unit (PMU) 221 in order to secure power functionality and powersaving mode. The PMU can handle either conductive or/and cable charging 220 of a rechargeable battery of the apparatus 20, e.g. in a docking station. The battery may be either of Lithium Ion type or Nickel Metal type or Lithium Polymer type.

The CPU 20 communicates with four different types of memory. Memory 1, ROM 23a; Memory 2, RAM 23d; Memory 3, FLASH 23b; Memory 4, Hard Disk (HD) 23c.

In more detail, the hardware of this embodiment comprises a first central processing unit 20; an AUX connection 21 for external connection functionality; an I/O input output functionality 22 as e.g. the above mentioned USB interface; the ROM memory 23a for read only capability, e.g. storing pre set apparatus functions; a Flash memory 23b for up gradable memory capability, a hard drive (HD) memory 23c for in apparatus memory storage capability; a pressure sensitive display 24 for visualization of functions, results of processed information, and for user input via pressure command capability; a video capability function 25 for motion picture capability i.e. instructions, recipes etc.; an audio function 26 for audio capability i.e. motion picture sound, radio, music, etc.; and an optional functionality capability 27, e.g. for connection of various external devices, such as a printer, barcode reader, memory stick, or similar. A Block 210 comprises the memories 23a-23d, the video unit 25, the audio unit 26, and optional units 27.

The video capability function 25 and the audio function 26 may provide multimedia capability of the apparatus 10. Alternatively, or in addition, a specific multimedia unit 29 may be provided. Thus, the apparatus may for instance process downloaded recipes; comprising comprehensive step by step cooking instruction videos; shopping lists for food; etc. in preparation of preparing food from food raw materials and in a preferred manner that is in compliance with the recommended lifestyle. The user may conveniently position the apparatus 10 in its docking station 10 in the kitchen where the food is to be prepared, thus leaving the hands of the user free for cooking activities.

All units of the apparatus 10 are operationally connected in a suitable way.

FIG. 2A is a schematic block diagram of a basic hardware setup of an apparatus according to an embodiment having double processors with split functionality.

This schematic drawing shows an electronic device 2B having two central processing units (CPU), enabling split functionality. Split functionality means that the different processors handle different Input and provide different Output, and that the processors are configured to executing control routines on each other (such as clock, speed, mathematical accuracy etc.).

A first block 210 comprises the memories 23a-23d, the video unit 25, the audio unit 26, and optional units 27.

The first CPU 230 is configured to provide Medical and Power Management functionality. The first CPU 230 is configured to communicate with the video unit 25, the audio unit 26, the memories 23a-23d, thus providing a Medical functionality, e.g. for patient critical tasks.

The second CPU 231 is configured to provide Multimedia and I/O. The second CPU 231 is arranged to communicate with the video unit 25, the audio unit 26, the memories 23a-23d, of a second block 210', as shown in FIG. 2, thus providing Multimedia functionality, e.g. for tasks that are non critical for the patient and its safety.

This embodiment 2B provides increased patient safety in comparison to the above described embodiment 2.

Figure 2C:
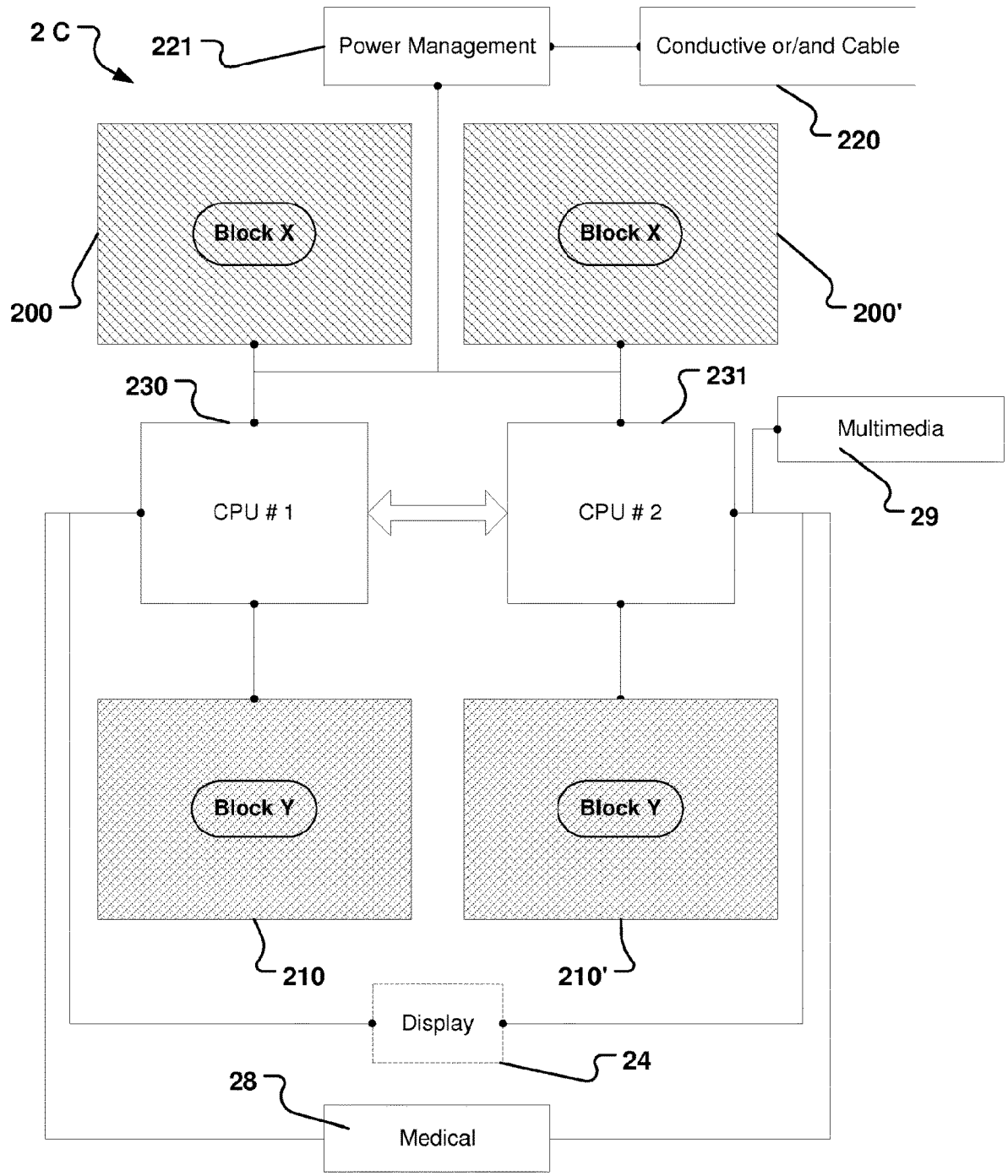
FIG. 2C is a schematic block diagram of a basic hardware setup of an apparatus according to an embodiment having double processors with mirror functionality.

FIG. 2C is a schematic block diagram of a basic hardware setup of an apparatus according to an embodiment having double processors with mirror functionality. Each of a first CPU 230 and a second CPU 231 comprises an I/O unit 200, 200', as well as a block 210, 210', as described above. This redundancy of components increases operational and patient safety. A power management unit 221 and a charge unit 220 provide for This schematic drawing shows an electronic device using two central processing units (CPU), enabling mirrored functionality. Mirrored functionality means, that the same processes are being executed simultaneously and checked that the CPU's delivers the same results and signals.

IF a master signal from the second CPU 231 is OK, then the display is run from the second CPU 231.

IF a slave signal from the first CPU 230 is OK, AND the master signal from the second CPU 231 is bad, then the slave signal from the first CPU 230 will be switched to the display 24.

With other words, the second CPU may take over the tasks of the first CPU, i.e. both CPUs are available for running patient critical applications, while only the second CPU provides the patient non-critical multimedia functionality.

This embodiment 2C provides increased patient safety and device reliability in comparison to the first described embodiment 2.

Figure 3:
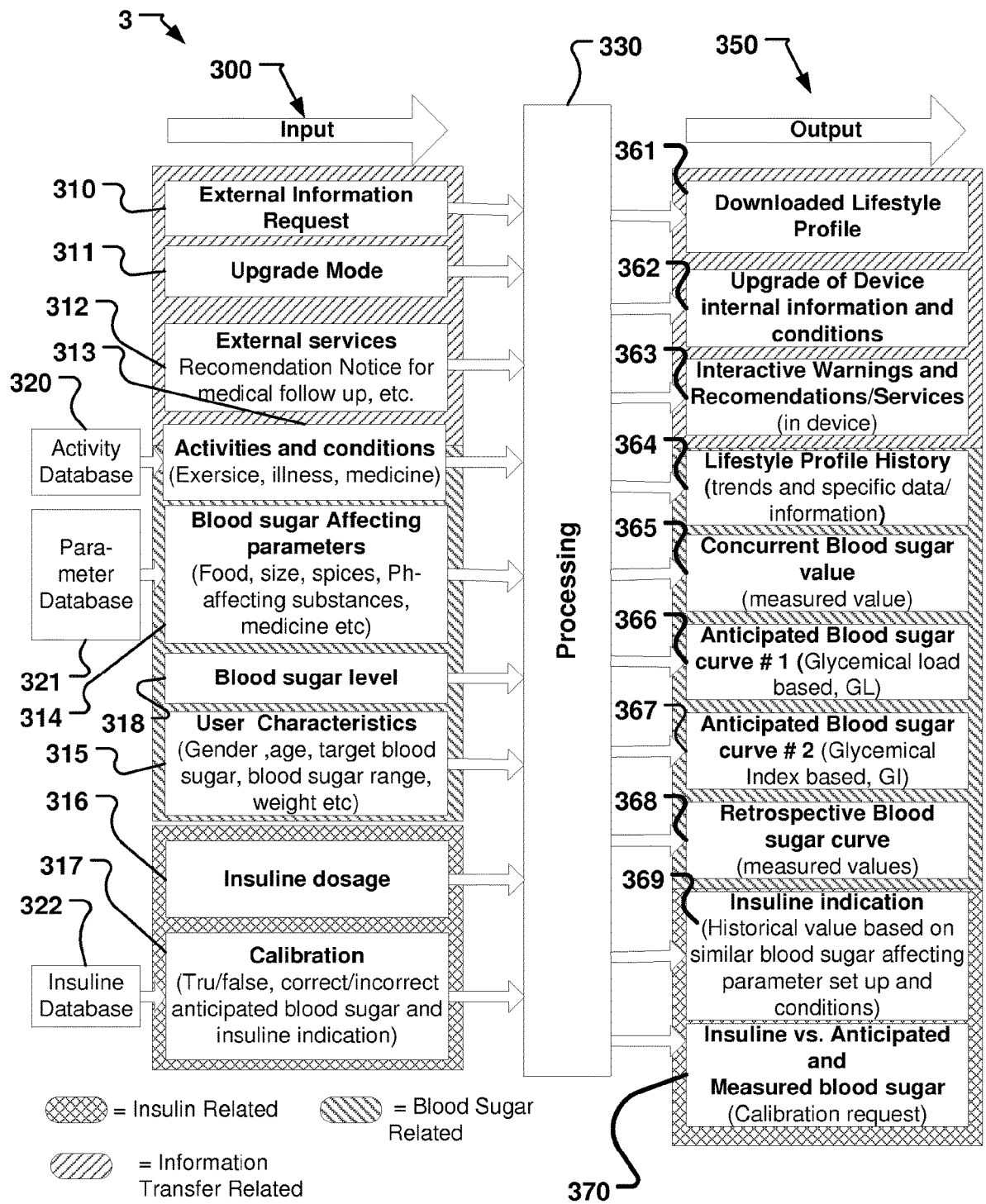
FIG. 3 is a schematic block diagram of information flows during processing in an apparatus or a method according to an embodiment.

FIG. 3 is a schematic block diagram of information flows 3 during processing in an apparatus 10 or a method according to an embodiment. FIG. 3 shows an information block diagram for typical glycemical calculation and retrospective information and controlling the apparatus 10.

Information input, either manually from a user, or via a signal is illustrated on the left in FIG. 3, as indicated by arrow 300. For processing 330, the apparatus 10 uses inputs 310-317 and blood sugar level 318, to calculate, compare and process information thereof, in order to present the output 350 described in the block diagram by the blocks 361-370. The processed information may also be stored, e.g. in HD memory 23c, for later use or retrieval. Information outputs, results and commands of the apparatus are depicted by arrow 350.

Insulin related inputs and outputs are grouped in FIG. 3, as well as Blood sugar related inputs and outputs, and information transfer related inputs and outputs.

Some specific, but not intended to be limiting, inputs will now be described in more detail.

310 External information request—e.g. via connection to external upgrade database (via Internet or GSM etc) requesting to automatically check the apparatus' 10 software (SW) status for available flash memory 23b download objects.

311 Upgrade mode—apparatus 10 is in a downloading mode for receiving upgradeable SW objects to flash memory 23b after external information request 310 is finalized. The result of upgrade mode 311 is an upgrade of the device internal information and conditions 362.

312 External services—the apparatus user receives recommendations or notice for medical follow up, sent from e.g. a medical specialist to the apparatus 10, (via Internet or GSM etc) and/or interactive warnings and recommendations 363, after downloading a lifestyle profile 361 created by the apparatus.

313 Activities and conditions—the user enters type of exercise, duration, intensity, health conditions such as illness, medication and other relevant information (i.e. time) needed to calculate 330 and create a lifestyle profile.

314 Blood sugar affecting parameters—the user enters food information such as type of food according to predefined food item lists, specific pre defined spices included in food or added to food, specific pre defined Ph-affecting substances included in food or added to food, and any medication ingested and other relevant information (i.e. time) needed by the apparatus to calculate 330 and create a lifestyle profile 361.

315 User characteristics—the apparatus 10 may be customized for the specific user by entering basic information such as: gender, age, targeted blood sugar, blood sugar range, weight, carbohydrate restrictions, medication and any other relevant user or other information, such as a time to be included in the calculation process 330.

316 Insulin dosage—the user enters in the insulin administration log the amount of insulin taken prior to a meal as well as the time to be included in the calculation process 330.

317 Calibration—the apparatus 10 enables the user to calibrate the input of insulin dosage 316 after the meal, by using an input after meal blood sugar level 318, and comparing this blood sugar value with the insulin dosage 316 in terms of true/false, correct/incorrect. The calibration is also performed by entering true/false, correct/incorrect for the anticipated blood sugar indication 366 and 367 to continuously fine tune and refine the apparatus calculation process 330.

318 Blood sugar level—the user may enter in the Blood sugar administration log a blood sugar value 365, prior to a meal and after the meal, to be included in the calculation process 330 and to enable calibration according to input 317.

320 Activity database—a pre defined database containing objects enabling inputs of activities and conditions 313. Activity database objects are upgradeable via the external information request functionality 310 and the upgrade functionality 311.

321 Parameter database—a pre defined database comprising objects enabling inputs of Blood sugar affecting parameters 314. Parameter database objects are upgradeable via the external information request functionality 310 and the upgrade functionality 311.

322. Insulin database, partly pre defined database information enabling inputs for Calibration 317 and may be continuously upgraded by the user via Calibration 317 and Insulin vs. anticipated and measured blood sugar 370 functionalities. Insulin database objects are partly upgradeable via the external information request functionality 310 and the upgrade functionality 311.

Some specific, but not intended to be limiting, outputs will now be described in more detail.

361 Downloaded Lifestyle profile—after the apparatus calculations are finalized, (based on 313-317, Blood sugar level 318 and 364-370), a life style profile may be uploaded to an external database or otherwise be transferred, e.g. to a medical specialist, health care provider, etc., in order to enable an External message 312 and Interactive warnings and recommendations 363. Furthermore, the life style profile receiver is thus enabled to e.g. prioritize patients, based on compliance/recommendations for notice for medical follow up. This provides, amongst others, a customized or specifically tailored advice to individual patients in order to maintain a recommended lifestyle; a screening of patient populations; and other services provided to the patient.

362 Upgrade of device internal information and conditions—a result of Upgrade Mode 311.

363 Interactive warnings and recommendations/services—warnings or recommendations may be based on analysis made in the apparatus 10, e.g. a specific food that the user wants to select is unsuitable or not in conformity with a recommendation, and more positive alternatives may be given; the warnings, recommendations or services may also be a result of an External Message 312 explained above.

364 Lifestyle profile history—a compilation of historical profiles (trends and specific data/information) created by the apparatus 10 for a meal, day, week, month, quarter etc stored in the hard drive memory and/or transferred via External information Requests 310 to an external database.

365 Current blood sugar value—by the user entered values connected to a specific event and stored in the apparatus' 10 hard drive memory 23c and may be made visible in the display as a display object, e.g. a blood sugar value, current and expected patient condition, and a trend curve. The Current blood sugar value 365 enables Insulin vs. anticipated and measured blood sugar 370 and Insulin dosage 317 block activities and commands.

366 Anticipated blood sugar curve #1—a glycemical load (GL) curve mainly based on 313 and 314 inputs, processed by 330 (calculating the combined effect of foods etc and the increasing or decreasing effect on the #1 curve). The Glycemic Load GL curve may be presented as a visualized glycemical load curve in the apparatus' 10 display 24.

367 Anticipated blood sugar curve #2—a glycemical Index (GI) curve mainly based on 313 and 314 inputs, processed by 330 (calculating the combined effect of foods etc and the increasing or decreasing effect on the #1 curve). The Glycemic Index GI curve may be presented as a visualized glycemical Index curve in the apparatus' 10 display 24.

368 Retrospective blood sugar curve—based on the user over time entered blood sugar values (via Blood sugar level 318) created curve, curve peaks and curve downturns are analyzable to see connections, relations and compliance to entered data i.e. 313, 314, 315, 316, 317.

369 Insulin indication, a functionality of the apparatus that when entered data for a i.e. a meal matches similar conditions (blood sugar affecting parameter 314 and activities 313 combinations vs. current measured blood sugar 365). The apparatus may immediately visualize in the display this relation and gives the user an insulin indication on what was by the user confirmed true/false, correct/incorrect insulin dosage at that time. This provides the user an aid to learn and to adapt, decrease, improve or render more effective his/her insulin dosage selection based on the user's lifestyle track record. This functionality provides for lowered insulin intake by the patient, resulting both in reduced health care costs and improved patient safety.

370 Insulin vs. anticipated and measured blood sugar—an automatic request from the apparatus 10 that enables the user to calibrate the input 316 after the meal by using after meal Blood sugar level 318 and compare this value versus the insulin dosage 316 in terms of true/false, correct/incorrect via 317 input functionality. The calibration request is also to performed calibration by entering true/false, correct/incorrect via the input functionality 317 for the anticipated blood sugar indication 366 and 367. This request is required to continuously fine tune and refine the apparatus calculation process 330.

Figure 4:
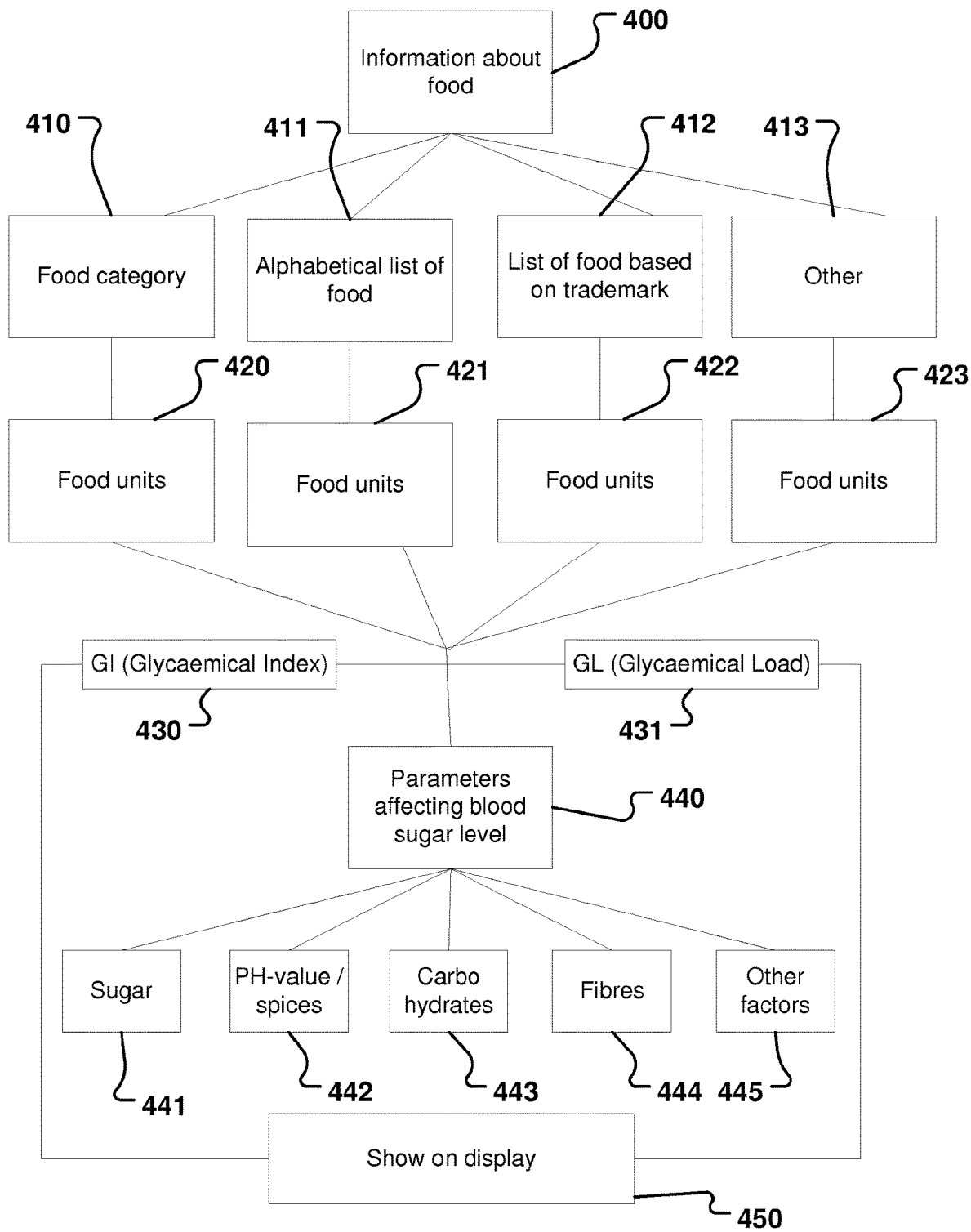
FIG. 4 is a schematic block diagram illustrating a structure for displaying processed glycemical indexes, glycemical loads and glycemical affecting parameters for different foods units.

FIG. 4 is a schematic block diagram illustrating a structure for displaying processed glycemical indexes, glycemical loads and glycemical affecting parameters for different foods units.

In FIG. 4 a schematic illustration of the functional blocks of an embodiment of the apparatus 10, of which a hardware setup is described above with reference to FIG. 2 and information flows are illustrated with reference to FIG. 3. The functional blocks illustrated in FIG. 4, comprise input information about food 400 from of a variety of in advance stored food parameters/units, automatic calculations of glycemical indexes, glycemical load and a variety of glycemical influencing parameters respectively.

For instance foodstuff units may be chosen in steps 420-423. The foodstuff units may be input in various manners. For instance, choices may be made between the in advance in the memory stored food parameters/units and for input of an amount of respective food parameter/unit. This may be based on food categories 410, alphabetical lists of foods 411, lists of foods based on trademarks 412, or other inputs, e.g. from a barcode of a food product packaging.

Other input parameters that affect the blood sugar level 440 comprise sugar 441, PH affecting preparations or spices 442, carbohydrates 443, fibers 444, or other factors 445.

Based on these information objects, a glycemical index 430 or a glycemical load 431 may be presented and shown on the display at step 450. Alternatively, or in addition, the processed information object updates the lifestyle profile and is available for further processing or later use.

Specific menu structures are illustrated in FIGS. 18A-F described in more detail further below.

The first central processing unit 20 may provide for calculation of summed up (combined effect) glycemical indexes and/or summed up glycemical loads for the select food parameters/units on the basis of the in advance stored information about glycemical indexes and/or glycemical load and the glycemical affecting parameters for respective food parameter/unit and the stored information about the amount of a selected food parameter/unit. Display 24 may provide for displaying the in advance stored food parameter/unit and the in advance stored information about respective food parameter/unit and for display of calculated summed up all (combined effect) glycemical indexes and/or estimated summed up (combined effect) glycemic load.

The electronic apparatus 10 is a portable electronic unit, or may be an integrated function in a cell phone or a part of a functionality of a cell phone, or a PDA (Personnel Digital Assistant) or similar, with software for handling of functions of embodiments. The apparatus may also be for the purpose particularly designed portable electronic unit with an input function and a display. Some examples of embodiments are illustrated in FIGS. 12 to 16 and described in more detail further below. Alternatively the apparatus is stationary, e.g. provided in the form of a computer apparatus adapted for executing a software thereon. Alternatively, or in addition, the apparatus 10 may be provided as an integrated unit that is implemented with other equipment, such as blood sugar measurement device, blood pressure monitors, etc.

The apparatus 10 includes a timer or a clock function for time measurement and time registration and the memory can be designed for storage of the central unit summarized blood sugar affecting factors, such as glycemical indexes (GI), and of the clock measured times and intervals in order to enable an over the time monitoring of the blood sugar affecting factors. Furthermore, the memory may include in advance stored recommended blood sugar affecting factors that the first CPU 20 calculates and summarizes, and compares with registered and calculated values.

A second CPU handles less patient critical functionalities, such as multimedia applications and data objects therefor.

Alternatively, information is stored for a preferred lifestyle, that is compared with registered and calculated values, whereupon processed or calculated information about the lifestyle of a user may be given. This may include, apart from for different food units stored information about Glycemic Index GI, Glycemic Load GL and glycemical affecting parameters, blood sugar affecting parameters, insulin dosage- and blood sugar value, physical activities, medication, diseases, body weight, Body mass index and nutrition related values for ingested foods/food units.

The central unit 20 may calculate intakes of net carbohydrates on the basis of registered information about ingested foods and with the aid of in advance in the memory stored information about gross carbohydrate and fibers. In this way, a more precise calculation may be made of the glycemical load and the blood sugar affecting factors.

The central unit 20 may be configured for summarization of glycemical load and glycemical indexed intake of food units, and for presentation of blood sugar affecting factors in the form of a glycemical conditions or relation. This results in a profile that, in combination with registered blood sugar values and registered insulin dosage, may be used to achieve a a) Retrospective analysis of the user's compliance in relation to recommended values or recommended lifestyle,
b) Concurrent analysis for a specific event or activity, and
c) Prognosticated analysis for a period ahead in time based on the trend of compliance against recommendations.

Thus, a user may, by means of the invention, in a simple and precise way adapt his/her insulin need or insulin dosage in order to achieve normoglycemical levels and to avoid episodes with hypoglycemia/hyperglycemia.

Tests of well-known technology for this purpose are uncertain and expensive. Therefore, a need for this type of prognosticating apparatus and method has existed with reference to the state of the art.

Embodiments of he invention may also be intended for the use of an apparatus to calculate the glycemical indexes and/or glycemical load for selected food units.

Moreover, a usage of the apparatus may be provided for monitoring of blood sugar affecting factors for an individual in relation to a registered blood sugar value and/or a registered insulin usage, and more precisely for monitoring of blood sugar affecting factors for an individual in relation to registered blood sugar values and/or registered insulin dosages. The apparatus may and summarize an individual's blood sugar related values over time in relation to recommended values.

Embodiments also comprise a method for electronic summarization of blood sugar affecting factors, comprising storing in a memory a majority of food units and glycemical indexes and/or glycemical load and a majority other glycemical affecting parameters for respective food unit; choosing by means of an input function between in the memory stored food units, and to register the amount of the food unit, respectively; calculating by means of a central unit summed up glycemical indexes and/or summed up (combined effect) glycemical loads for the select food units on the basis of the in advance stored information about the glycemical indexes and/or glycemical load and the glycemical affecting parameters for respective food unit and the registered information about the amount of the select food unit; and visualizing on a display the in advance stored food units, the in advance the stored information about respective food unit and for visualization of calculated summed up (combined effect of) glycemical indexes and/or estimated summed up (combined effect of) glycemical loads.

The method may also include the steps of calculating summed up (combined effect of) glycemical indexes with the aid of the glycemical affecting parameters in form of contents of sugar, carbohydrates, fibers, proteins and fats, stomach emptying time, digestion and absorption of carbohydrate in the small intestine, sugar types, starch types, production and cooking processes and others glycemical affecting parameters, such as the above mentioned meal times, physical activities, health condition, medication, etc.

The method may also include the steps of carrying out a monitoring that extends over a certain time, and based on that compile a blood sugar related trend in relation to in the memory stored and recommended values, and compiling the glycemical load and glycemical indexed intakes of food units, and calculating blood sugar affecting factors in the form of a glycemical state or condition, and relating the calculated blood sugar affecting factors with registered blood sugar values and registered insulin dosages.

Furthermore, the method may include the step to carry out a prognosis ahead in time, based on a compliance trend in relation to recommended values, for an adaptation of an insulin dosage. The method may also include the step of calculating a net carbohydrate intake based on the in advance stored information about the food unit's gross carbohydrates and fibers.

An aspect of the invention is that apparatus 10 may provide the possibility of electronically summarization of blood sugar affecting parameters for a user/individual.

Embodiments of the apparatus may by advantage be used by a diabetic person, persons practicing sports, persons that desire to loose weight and others as have an interest of monitoring and analyzing their blood sugar related values.

One implementation of the invention is a portable electronic unit, such as a mobile phone or a part of a functionality of a mobile phone, or a PDA (Personnel Digital Assistant) or similar, with a software for handling the functions of the invention. The invention may also be implemented as a specifically designed portable electronic unit with a display that enables simple registration into the invention. This facilitates registration of food intake and other values/factors and activities for the user. An alternative design is a stationary electronic unit, such as a person computer or similar, with software for handling the functions of the invention.

The apparatus includes a memory for storing data, input function, a central unit to be able to store and process information and a display to present information. The memory is for example a conventional computer memory or corresponding, input function such button, a pressure sensitive display, computer mouse or similar. The display for example is a pressure sensitive display LCD, or similar. One other design of the invention includes a timer for measurement and registration of point in time for and intervals in time between different events.

The memory contains a number of pre stored food units and other blood sugar affecting substances, and glycemical indexes (GI), glycemical load (GL) and glycemical affecting parameters for each food unit. The pre-stored information about GI and Glycemic Load GL is table values for each food unit. The glycemical affecting parameters includes information about food unit contents, such as carbohydrates (Kh), fibers, protein, fat, sugar content etc. The glycemical affecting parameters may also include information about food unit characteristics, such as type, maturity, fermentation, and processing information about the food, such as heating, fermenting, grinding, production, cooking. The glycemical affecting parameters include also for example information about contents of spices, such as cinnamon, clove, turmeric, salvia, garlic, pepper, pepper fruits, and pH lowering additives, such as lemon, vinegar, acidity (PH value) of food, and other food additives, such as for example magnesium, chrome, caffeine, fibers etc, that have a blood sugar lowering effect. Alcohol is a further parameter that affects the blood sugar level and may be considered by apparatus 10.

In addition or alternatively, an embodiment may comprise information objects about other glycemical affecting parameters, such as stomach emptying time, digestion and absorption of carbohydrates in the small intestine, type of sugar and characteristics of present starches, whether the starch is branched or straight. The glycemical affecting parameters, according to yet another design of the existing invention, also include information about earlier consumed substances and food units; previous meals may affect glycemical indexes for later consumed food units. The invention includes a number these glycemical affecting parameters in order to achieve a satisfactory result. Naturally, with reference to the summary of Glycemic Index GI, Glycemic Load GL and other blood sugar affecting parameters, it is of greater benefit to include as many of the glycemical affecting parameters as possible.

A number of food units are stored in the memory to establish a food unit data base; here the food units are organized in at least one list. Preferably the food units are organized for accessibility through multiple lists, such as a first list, a second list and a third list. In the first list is for example food units organized after food categories, i.e. after a hierarchical system with central categories that meat, breads, vegetables, etc. In the second list the food units are organized alphabetically units beginning with the letter A is organized under the letter A and food units beginning with the letter B is organized under the letter B. In the third list the food units are organized after trademark. One execution of the invention includes possibility for storage of a list of the user's favorites. The lists are designed so that they can be updated by for example manual input or through connection to a central database via the Internet or in other ways. One version of the invention the memory can be used for storage of the physical data of the individual, such as weight, body mass index etc.

An input function is performed in order to enable choices of food units pre stored in the memory, in order to allow input of further information, such as a blood sugar value and/or one insulin related value for the individual. By the input function the user can also enter information about body weight, exercise, diseases, medication and other activities or conditions.

Through embodiments of the invention, a user may obtain information about Glycemic Index GI, Glycemic Load GL and glycemical affecting parameters for each food unit, as being shown in FIG. 4. FIG. 4 shows schematic a block schedule for visualization of information about Glycemic Index GI, Glycemic Load GL and certain glycemical affecting parameters for different food units. Thus, a user may via the input function enter an optional list of food units, choose a food unit and to receive information about Glycemic Index GI, Glycemic Load GL and/or optional glycemical affecting parameter on the display.

The apparatus 10 includes also a central unit 20 for calculation of total Glycemic Index GI/Glycemic Load GL for selected food units on basis of the pre-stored information about Glycemic Index GI/Glycemic Load GL and the glycemical affecting parameters for each food unit and the entered information about amount of selected food units. Thus, the central unit is designed to use the pre-stored table values on Glycemic Index GI/Glycemic Load GL and calculate an actual Glycemic Index GI/Glycemic Load GL or a Glycemic Index GI/Glycemic Load GL that is closer the actual Glycemic Index GI/Glycemic Load GL using glycemical affecting parameters for each provision and any other glycemic affecting parameters. Thus, the blood sugar related value is summarized with regards to glycemical affecting parameters, and a corrected Glycemic Index GI/Glycemic Load GL for each food unit in for example a current meal, or a corrected Glycemic Index GI/Glycemic Load GL of totally consumed food units, e.g. a corrected Glycemic Index GI/Glycemic Load GL for the meal. Thus a more correct glycemical index is achieved for most of the consumed or selected food units, since the characteristics of the food units interact with each other and affect the resulting or total glycemical indexes.

In an embodiment the central unit 20 is configured for calculation of pre-stored information of Glycemic Index GI and glycemical affecting parameters for selected food units in relation to entered blood sugar values for the individual and/or the individual's insulin dosage, and thereby compiling the blood sugar affecting factors for the individual. For example the compiled blood sugar affecting factors are interrelations between the pre-stored information of Glycemic Index GI/Glycemic Load GL and glycemical affecting parameters for the selected food units, measured blood sugar value and insulin dosage. Alternatively, the central unit 20 is configured for processing calculated Glycemic Index GI/Glycemic Load GL in relation to the entered blood sugar value and/or insulin dosage in order to compile the blood sugar affecting factors for the individual. The compiled blood sugar affecting factors are for example shown on the display 24 as tables or graphs, enabling the user in a simple way to monitor his/her blood sugar affecting factors.

Figure 5A:
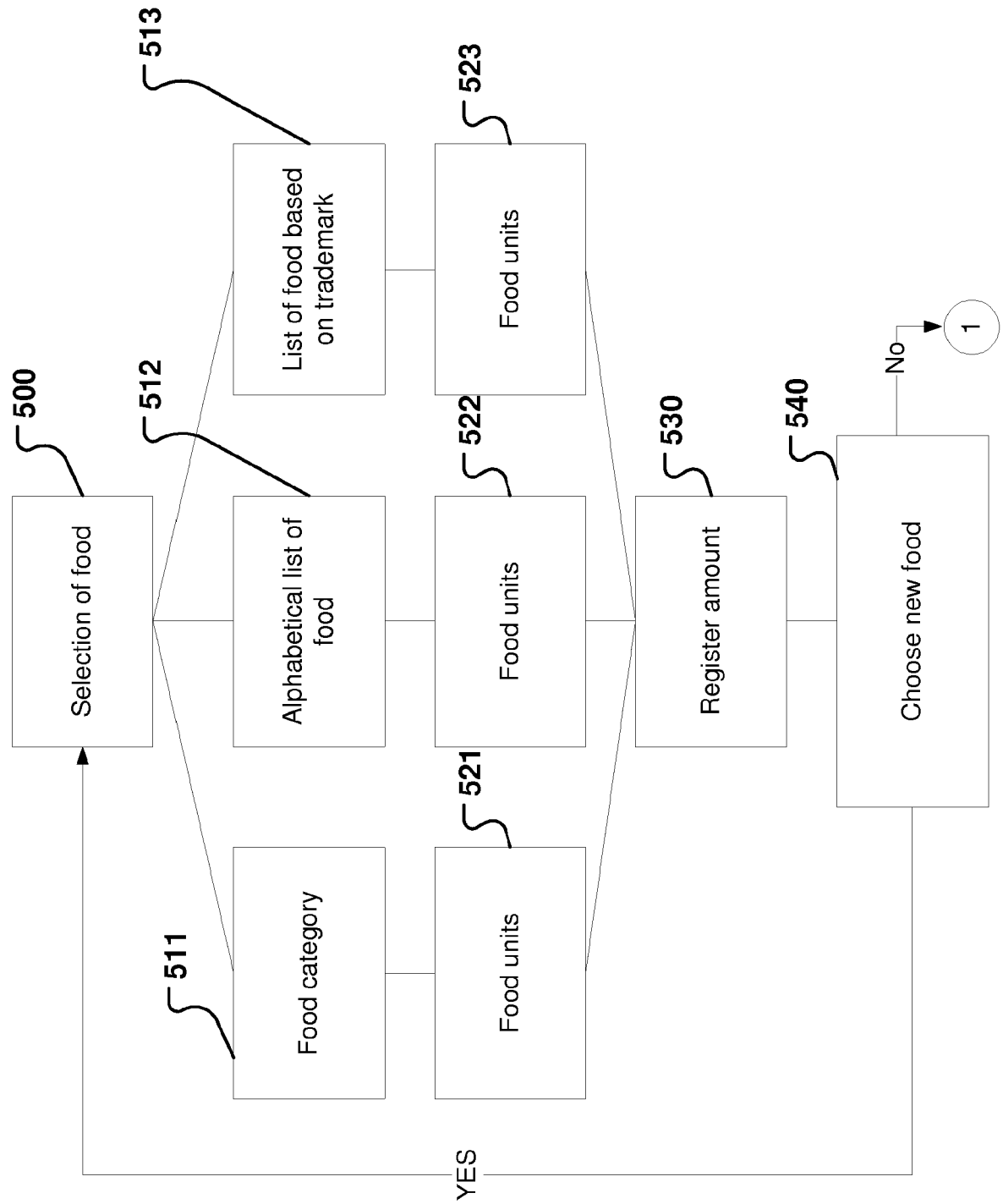
FIGS. 5A and 5B are linked schematic block diagrams that illustrate compilations of blood sugar affecting factors on the basis of selected food units and other blood sugar affecting parameters.
Figure 5B:
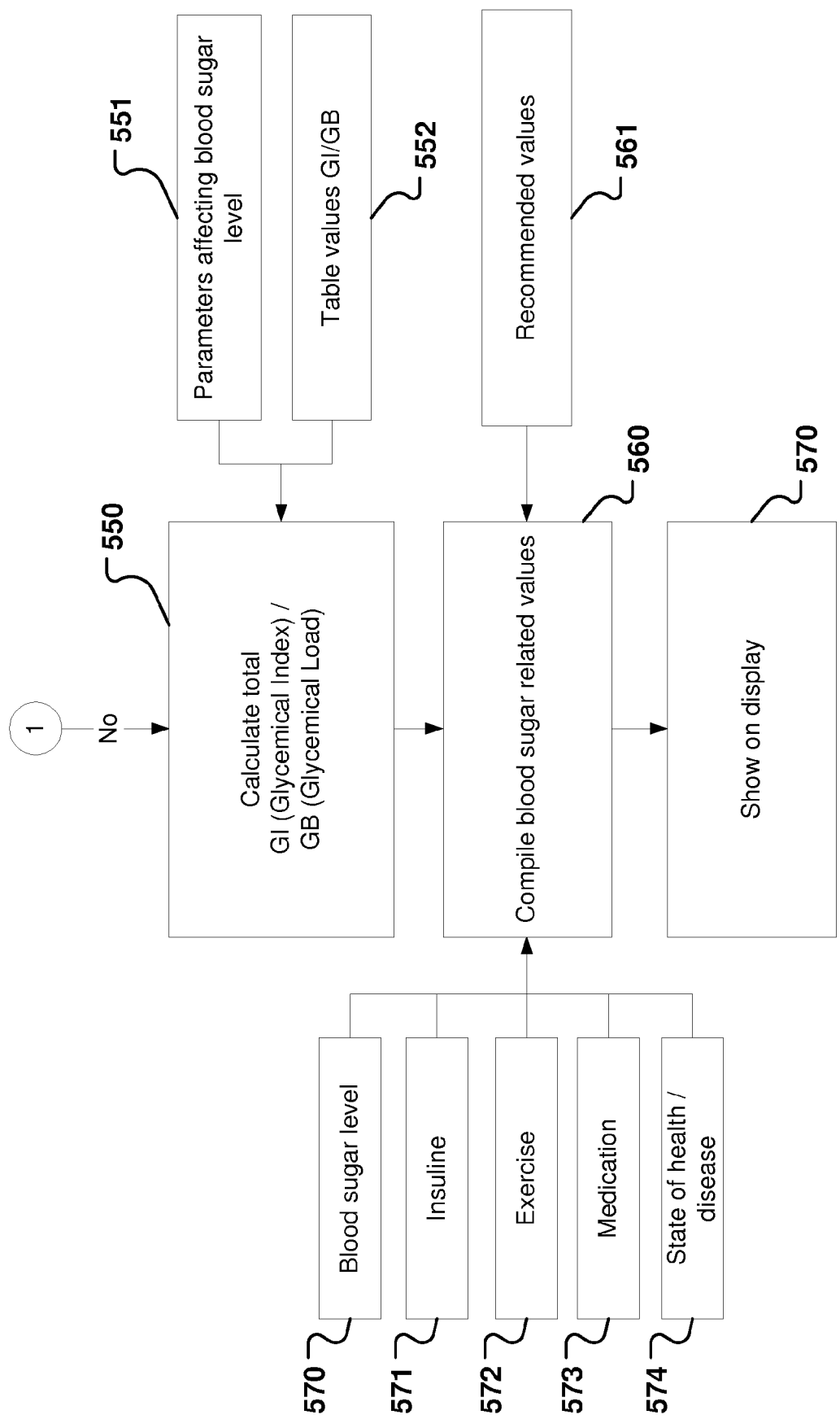

FIGS. 5A and 5B are linked schematic block diagrams that illustrate compilations of blood sugar affecting factors on the basis of selected food units and other blood sugar affecting parameters. A user selects 500 food units 521, 522, 523 according to the procedure illustrated in FIG. 5A from a food category 511, an alphabetical list of food 512, or based on a trademark 513. Furthermore, the user enters the amount 530 of selected food unit and chooses either new food units or completes input of food units <at step 540.

As illustrated in FIG. 5B, Glycemic Index GI/Glycemic Load GL for food units is calculated in step 550 with regard to the glycemical affecting parameters, whereupon an actual total Glycemic Index GI/Glycemic Load GL is received, added to and processed along with the entered blood sugar value and/or entered blood sugar affecting parameters for summarization of the blood sugar affecting factors. The blood sugar affecting parameters include information about for example whether the person is healthy or ill, health condition 574, sleep, blood pressure, insulin dosage 571, exercise 572 and others physical activities, medication 573 or alcohol intakes or different combinations thereof. According to an embodiment the compiled blood sugar affecting factors are compared to recommended values 561, e.g. values recommended by a doctor or a lifestyle recommended by a doctor. The compiled blood sugar affecting factors 560, possibly in relation to the recommended values are presented on the display in step 570, for example in form of a profile, indication, traffic light warning, recommendations, table, and/or graph, numeric or in another appropriate way.

According to an embodiment glycemical loads and glycemical indexes for consumed substances are combined in order to analyze glycemical peaks, relations and conditions during a time frame for an individual. This may be combined with registered blood sugar values and insulin dosage with the blood sugar affecting factors to form a blood sugar related profile.

The profile may with advantage be used for a retrospective analysis of compliance with issued recommendations. The profile may also be used for concurrent analysis of a specific sequence, as consumption of food units or other substances, a condition etc. The profile can also be used for a prognosticated analysis for a period in the future, based on the trend of compliance to recommended values or a recommended lifestyle, allowing a more precise adjustment of the insulin dosage. In this way a tailored and more exact dosage of insulin is provided in order to achieve normoglycemia and to avoid episodes with hyperglycaemia and hypoglycaemia.

According to an embodiment the central unit 20 is configured for calculation of intakes of net carbohydrates using the pre-stored information in the memory, about a food units gross carbohydrate content and fiber contents or fiber density, where net carbohydrates corresponds to gross carbohydrates minus fibers and other carbohydrates that do not affect the blood sugar value. Thus glycemical indexes, glycemical load and net carbohydrates may be calculated and presented in relation to the individual's blood sugar value and/or insulin dosage. Furthermore glycemical indexes, glycemical load and net carbohydrates may be calculated and presented in relation to the individual's blood sugar value and/or insulin dosage combined with entered information about medication, exercise and/or health condition, whereas the resulting values may be compared to the recommended values and presented in an appropriate way on the display.

One example of registered parameters during a day is shown in the table below.

| Category | Meal 1 | | | | | |
|---|---|---|---|---|---|---|
| (breakfast) | Meal 2 | | | | | |
| (lunch) | Meal 3 | | | | | |
| (snack) | Meal 4 | | | | | |
| (dinner) | Meal X | Total | | | | |
| Provisions | Which | Which | Which | Which | Which | A |
| Carbohydrates | Quantity | Quantity | Quantity | Quantity | Quantity | B |
| Fat | Amount | Amount | Amount | Amount | Amount | C |
| Fibers | Amount | Amount | Amount | Amount | Amount | D |
| GI-value | Value | Value | Value | Value | Value | E |
| GL-value | Value | Value | Value | Value | Value | F |
| Measured blood sugar value | Value | Value | Value | Value | Value | G |
| Insulin dose | Dose | Dose | Dose | Dose | Dose | H |
| Condition (Healthy/ill) | Condition | Condition | Condition | Condition | Condition | I |
| Body Weight | Value | Value | Value | Value | Value | J |
| Medication | Value | Value | Value | Value | Value | K |
| Other | Other | Other | Other | Other | Other | L |
| Summary | X | Y | Z | XX | YY | TREND |

Registered and processed values and factors are stored in the memory and an analysis may be performed after a meal time, after a day, weekly, monthly etc, and also to achieve a future prognostication, as has been described above. In total this gives an easy to grasp overview as the results may be presented in various ways and may in a simple way show for example a diabetic's behavior in relation to the recommended lifestyle.

Figure 6:
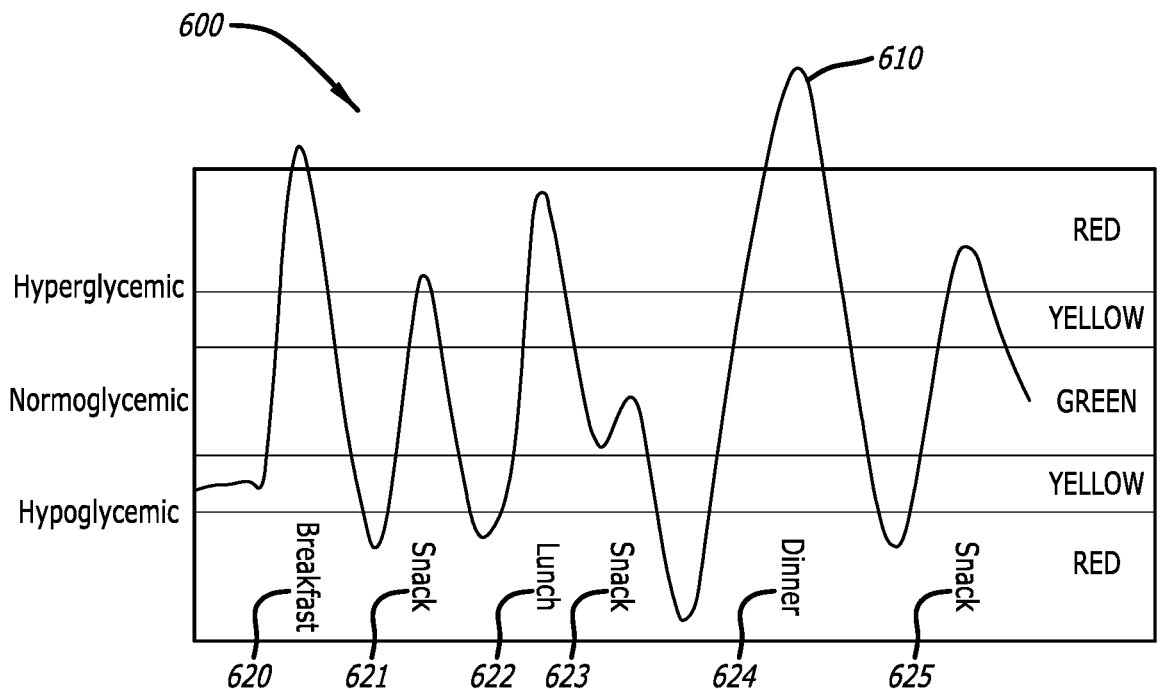
FIG. 6 is a schematic illustration of a graphical user interface of a screen of an embodiment.

FIG. 6 is a schematic illustration of a graphical user interface 600 of a screen of an embodiment. More precisely, FIG. 6 shows an example of visualization of a blood sugar indicative curve 610 in the apparatus' 10 display 24 in a one day viewing scale, or as a retrospective blood sugar curve. The blood sugar indicative curve 610 may be visualized as an anticipated blood sugar curve based on glycemical load 366, which above was mentioned as curve #1 in FIG. 3. Alternatively, or in addition, the blood sugar indicative curve 610 may be visualized as a glycemical index based curve 367, which above was mentioned as curve #2 in FIG. 3. The curve may also be visualized as an retrospective blood sugar curve 368 based on measured values.

The graphical user interface 600 further comprises the following elements:

620—An indicator for a meal time called breakfast. With connected calculated values 610 creating a curve related to the mealtime;

621—An indicator for a meal time called snack With connected calculated values 610 creating a curve related to the mealtime;

622—An indicator for a meal time called lunch. With connected calculated values 610 creating a curve related to the mealtime;

623—An indicator for a meal time called snack. With connected calculated values 610 creating a curve related to the mealtime;

624—An indicator for a meal time called dinner. With connected calculated values 610 creating a curve related to the mealtime;

625—An indicator for the meal time called snack. With connected calculated values 610 creating a curve related to the mealtime.

Figure 7:
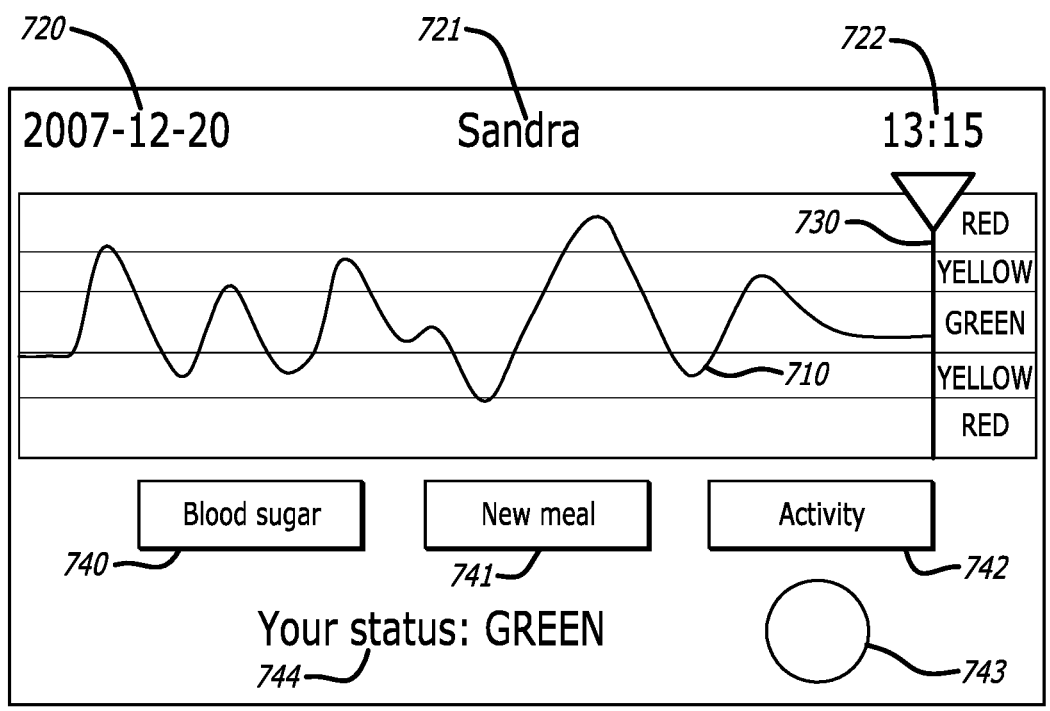
FIG. 7 is a schematic illustration of a graphical user interface of a screen of an embodiment showing a current status of a user.
Figure 8:
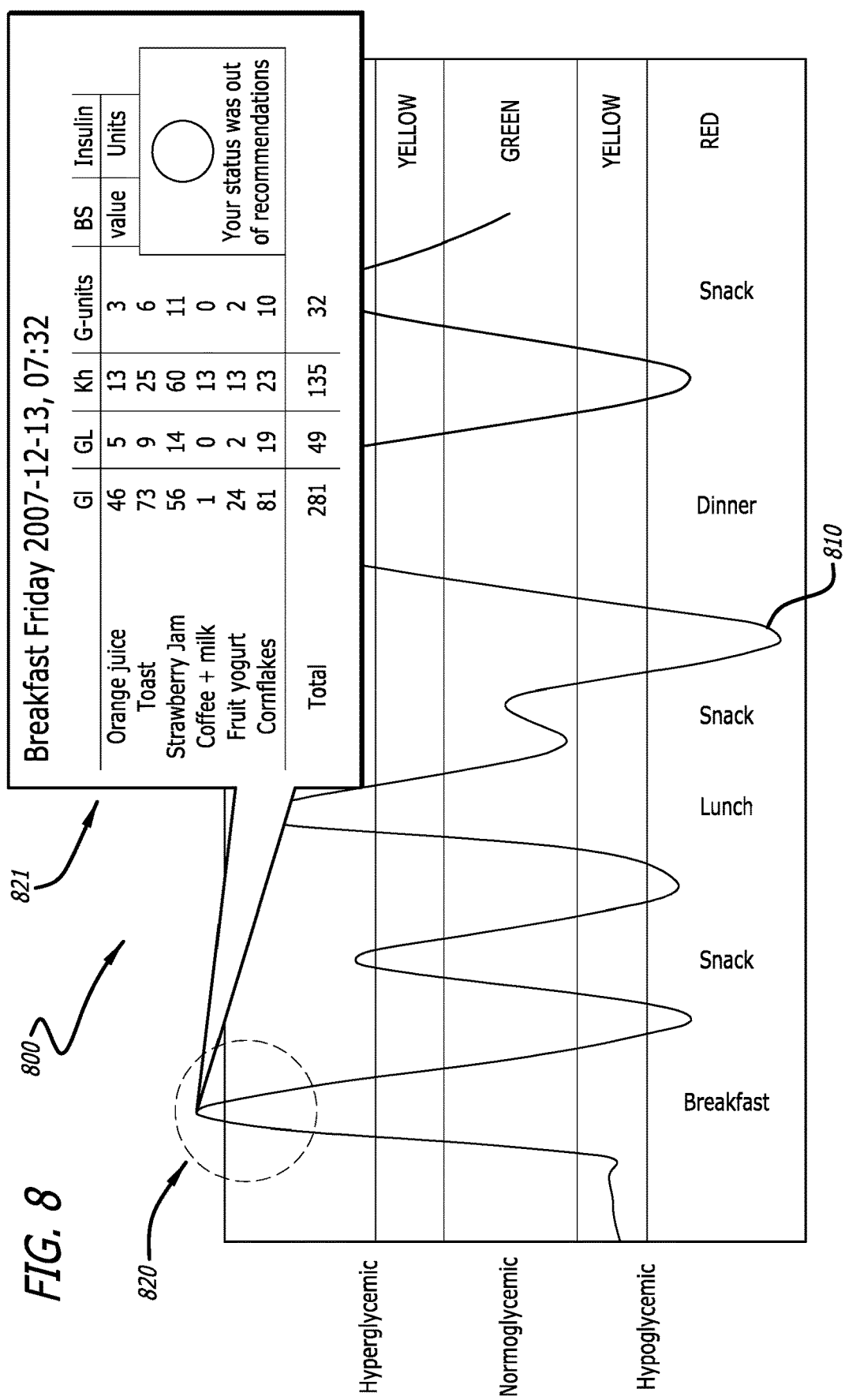
FIG. 8 is a schematic illustration of a graphical user interface of a screen of an embodiment showing a historical status of a user at a selected point in time.

A range of normoglycemic blood sugar values is visually indicated by a green band, extending towards red bands indicating hyperglycemic and hypoglycemic ranges, respectively, with intermediate yellow bands. (The bands in FIGS. 6-8 are merely labeled with their colors due to the black and white nature of the Figures. One skilled in the art will understand that the actual display may use colors instead of labels.) Thus, the user may at a glance be able to identify the blood sugar circumstances over time. Based on a pressure sensitive screen of display 24, the user may pick selected points or regions on the curve and receive further information or recommendations related to that point or region, as will be shown with reference to FIG. 8 below.

FIG. 7 is a schematic illustration of a graphical user interface 700 of a screen of an embodiment showing a current status of a user. A blood sugar curve 710 is shown, similar to the curve 610 shown in FIG. 6. Furthermore, the graphical user interface 700 comprises a date field 720, e.g. for indicating current year, month and day or in an different other order depending on configuration; a user configurable field 721, e.g. for an indication and an option for the user to personalize the apparatus, the example shows an apparatus for a person named Sandra; a time field 722, e.g. for an indication of the current time (clock), depending on configuration this may be shown differently (am/fm); a time bar 730, as an indicator of the current time on the curve in relation to the time field 722; a first button 740 on the pressure sensitive touch screen indicative for blood sugar, pressing the button enters blood sugar registration mode in the apparatus 10; a second button 741 on the pressure sensitive touch screen indicative for New meal, pressing the button enters new meal registration mode in the apparatus 10; a third button 742 on the pressure sensitive touch screen indicative for Activity, pressing the button enters activity registration mode in the apparatus 10; a status indicator 743, here in the form of a traffic light indicator, displayed as a green circle in the display if the user is in compliance, yellow circle if the user is slightly out of compliance and red circle if the user is out of compliance; and a status indication text 744, following the same Traffic light indicator principle as status indicator 743 but in text instead, perhaps also color coded similar to the latter.

FIG. 8 is a schematic illustration of a graphical user interface 800 of a screen of an embodiment of apparatus 10, showing a historical status of a user at a selected point in time. A blood sugar curve 810 is shown, similar to the curve 610 or curve 710. Once the user presses on a certain point or region of the curve 810, as visualized by the circle 820 in FIG. 8, an information box 821 appears in the apparatus display. The information box 812, appears in the apparatus display for instance if the user presses on a curve peak, as shown in FIG. 8. The information box 821 visualizes the combined effects behind the curve peak; the drawing only shows a fraction of what may be displayed as an example to show the principle in this example: Food unit/intake, glycemical index values (GI), glycemical load values (GL), net carbohydrates (Kh), Glycemical units (an apparatus unique system for handling restrictions of food units according to recommendations, compare to points system used by e.g. by The Weight Watchers), Blood sugar value (BS) and insulin. The box 821 also includes traffic light indicator according to principle described above with reference to status indicator 743 and status indication text 744 according to the principle described above. The box 821 also clearly states a meal type (i.e. breakfast), date and time of the day.

Figure 9A:
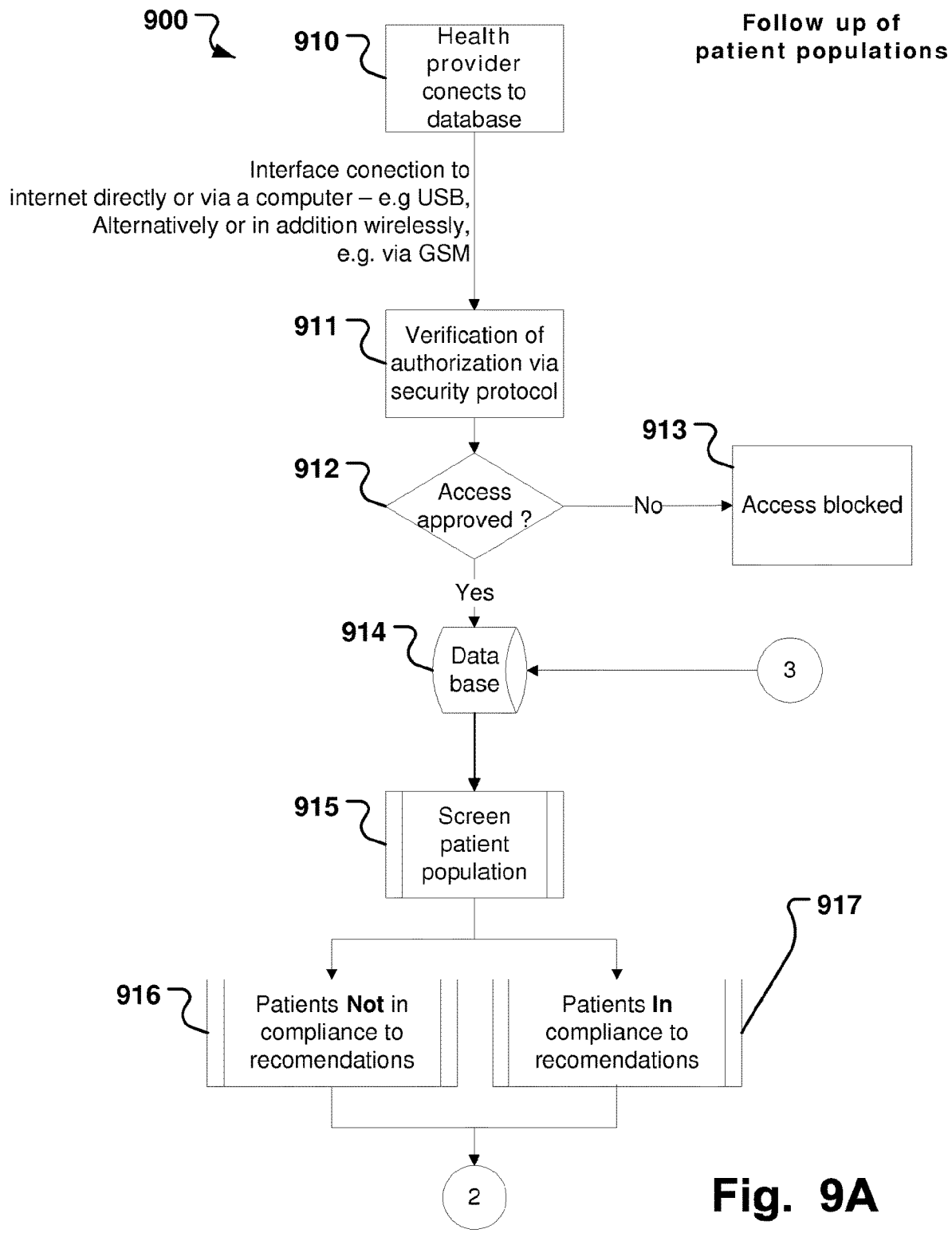
FIGS. 9A, 9B, 9C are linked schematic block diagrams illustrating follow up of patient populations.
Figure 9B:
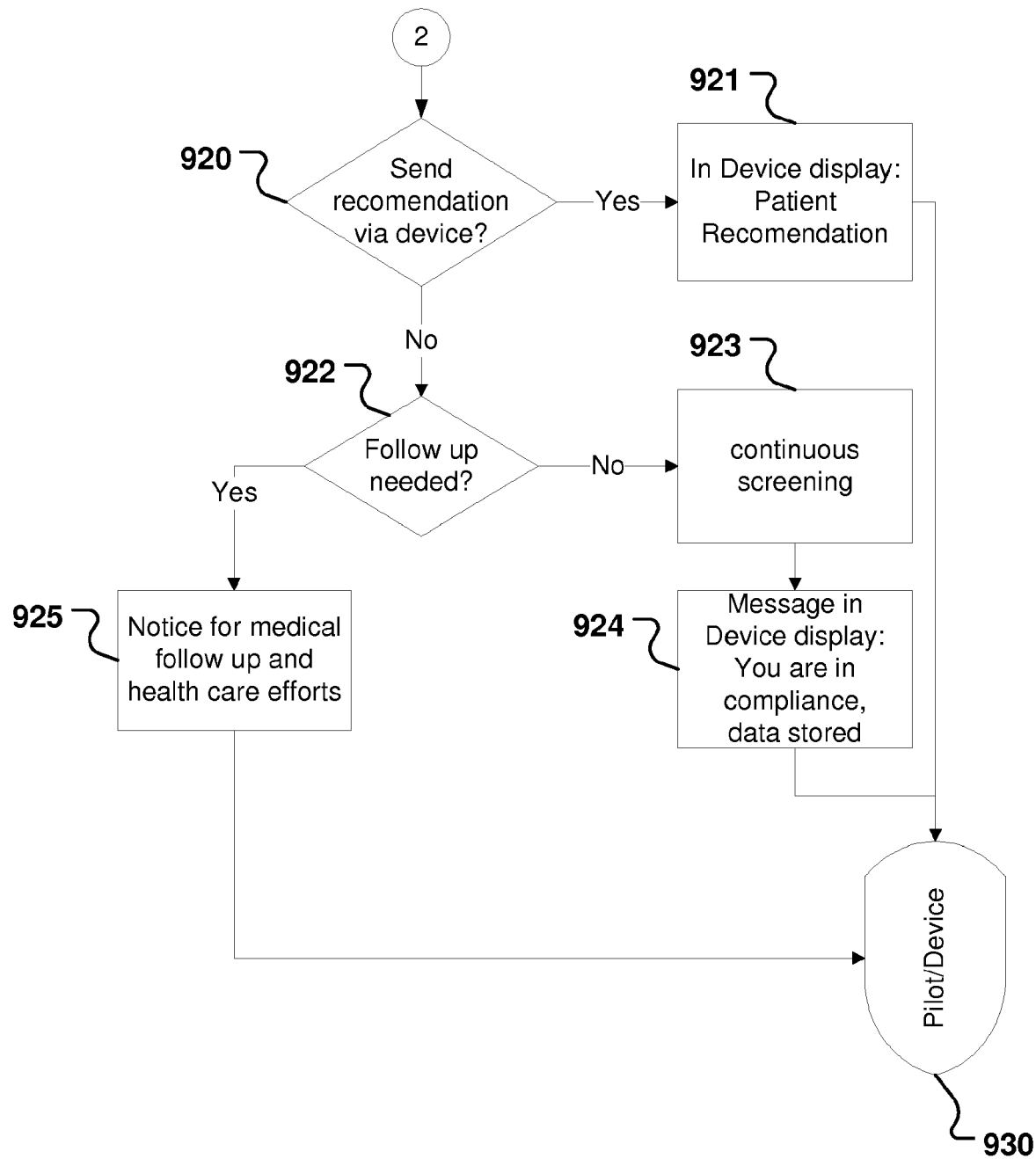
Figure 9C:
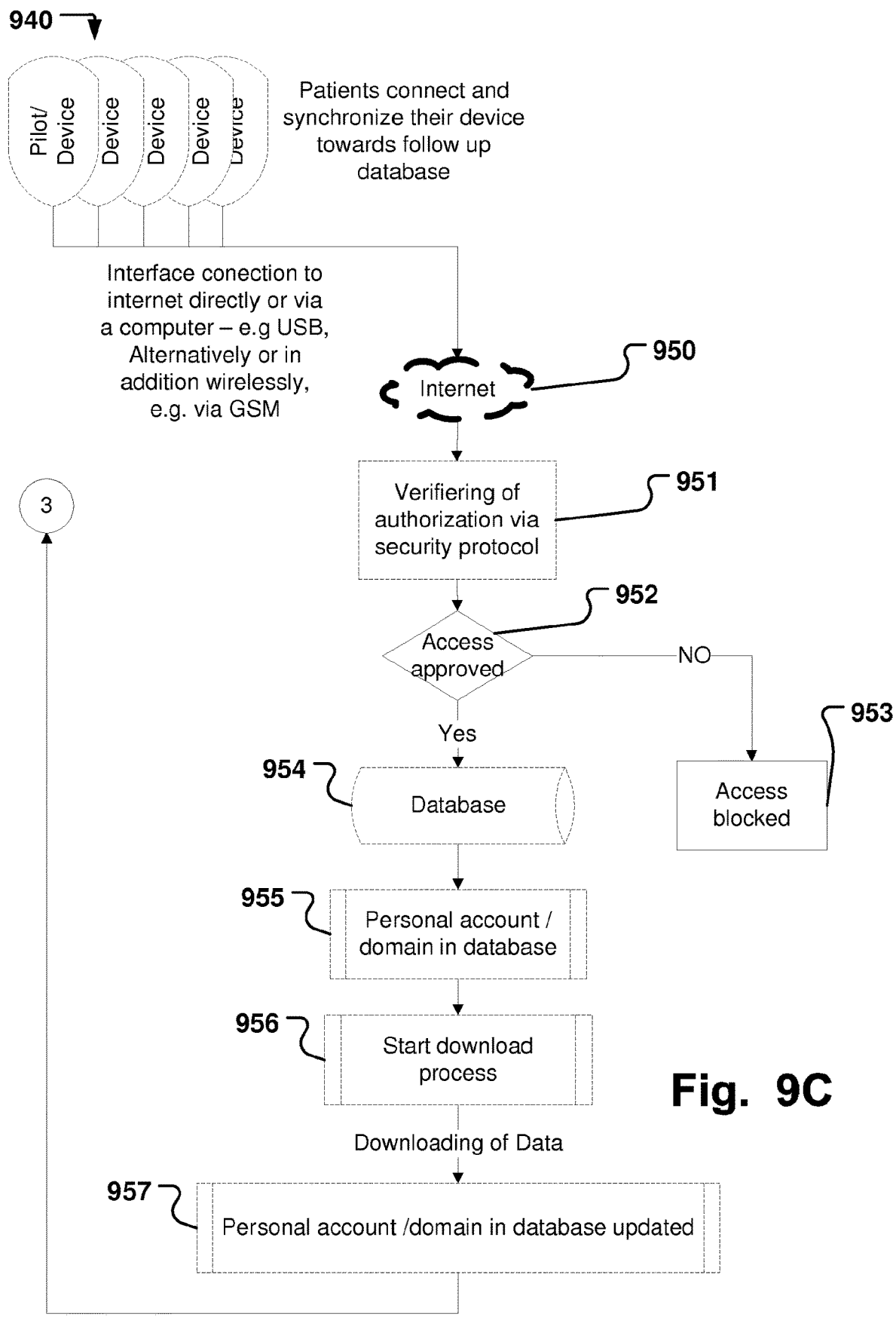

FIGS. 9A, 9B, 9C are linked schematic block diagrams illustrating a follow up 900 of patient populations by means of a system comprising a plurality of the above described apparatuses 10. According to an embodiment of follow up 900 of patient populations, a method, computer program and/or system comprises a plurality of steps and/or features 910 to 957, which are elucidated in detail hereinafter. A health care provider connects 910 to a data base. For instance a medical professional of the health care provider enters a database 914 specially configured and to be used by a plurality of apparatus' 10 users, such as diabetic patients, to download their lifestyle profiles. In order to provide a secure access to the database 914, a verification 911 of authorization may be performed via a security protocol. This prevents unauthorized access to the database 914. In case access is approved at step 912, the database 914 is accessible by the health care provider. In case access is denied, and the requested access to the database 914 is blocked, as illustrated by block 913, due to authorization unconformity.

The database 914, is specially configured to be used by a plurality of the apparatuses 10 users to download their lifestyle profiles and for a health provider to follow up his or her patient population, i.e. a multitude of users/patients.

The database 914 provides the health care provider to screen 915 the patient population. Screening 915 is a functionality mode offered by the database 914 that enables the health care provider to follow up his or her patient population. The process uses the principle that all patients in compliance with selected health criteria, are separated from patients outside of compliance, i.e. in nonconformity with the selected health criteria or recommendations. The health criteria may for instance be a certain level of hypoglycemia or hyperglycemia. Deviations from this level are for instance identified by thresholding a patient's current, mean or historical values.

Patients not in compliance 916 to recommendations, are for instance selected by being out of a recommendation span, when no information is registered at all, or gaps exist in their lifestyle history registration track.

Patients in compliance 917 to recommendations, are for instance selected by being within the recommended span, no information is missing or no gaps exist in their lifestyle history registration track that was uploaded to database 914.

As illustrated in FIG. 9B, the health provider may communicate with the users of the apparatuses 10. For instance, recommendations may be send 920 to the apparatuses 10 for noticing the users thereof of certain conditions, recommendations, etc. The health provider may use the database functionality of screening 915 for selecting patients that are in non-compliance and to only send recommendations to the apparatus/device 930 of the selected patients. Apparatuses 930 are of the type of apparatus 10 described above.

In the device display (24) of the apparatus, unique recommendations are communicated to the user by the health provider in step 921, e.g. to the selected patients that are in non-compliance with recommendations.

A decision to be taken by the health provider if a follow up 922 is needed, may be based on the database 914 functionality to send notice for medical follow/health care efforts to the patient/user via the apparatus/device 930. the decision may be automatically taken by selected criteria, such as if a reply of a user is received, or if the user follows recommendations sent to him/her, which is identifiable by a patient that was in non-compliance with recommendations transferring into compliance with recommendations.

In case no follow up is needed, a continuous screening 923 is made, i.e. if the decision is taken to not follow up the patient, the patient/user will be screened continuously by the database 914 by uploading of the subsequent lifestyle profiles in time. Alternatively, or in addition, a message in the display of the device 930, may be provided that the user is in compliance, and the data stored. No further action is required by the health provider or the patient, his/her lifestyle is in compliance.

In case a follow up is needed, a notice for medical follow/health care efforts is send to the device 930 and communicated to the user on the display. This functionality enables the health provider to use the database 914 functionality to send a notice for medical follow/health care efforts to the patient/user via the apparatus/device 930. The patient may for instance be requested to visit his doctor and an appointment time may automatically be booked, e.g. by synchronizing a calendar functionality of the doctor and the patient.

As illustrated in FIG. 9C, the population (multitude) of user/patients with a multitude 940 of apparatuses 930 synchronizes their apparatus/device towards a follow up database 954. Follow up database 954 may be integrated in database 914. Communication may occur via an Internet connection 950 via each of the apparatuses 930, via an intermediate computer, directly via a cable interface, such as USB, or wirelessly via Bluetooth, GSM, WLAN, etc.

A verification 951 of authorization is provided via a security protocol, in order to prevent unauthorized access to the data base 954. Once access approved at step 952, the requested database access is granted. Otherwise, the access is blocked 953, whereby the connection to the database is blocked for the person that requested access due to authorization unconformity.

The database 954 is specially configured to be used by the apparatus 930 users (patients) to upload their lifestyle profiles and for a health provider to follow up his or her patient population (multitude of users/patients) and download data objects to the database or to upload data objects to the device 930.

The database 954 has different personal accounts/domains 955 that comply with the patient/user identity data. The lifestyle profile is downloaded to this personal account/domain and the apparatus/device 930 is enabled to synchronize for messages or downloads etc.

Starting 956 a download process, the database and the apparatus/device communicates and the data objects are transferred from the apparatus/device to the database and to the patients/users personal account/domain.

The personal account/domain in the 954 database is updated at step 957, whereupon the download process is completed and the data objects are transferred from the apparatus/device to the data stored database 914.

Figure 10:
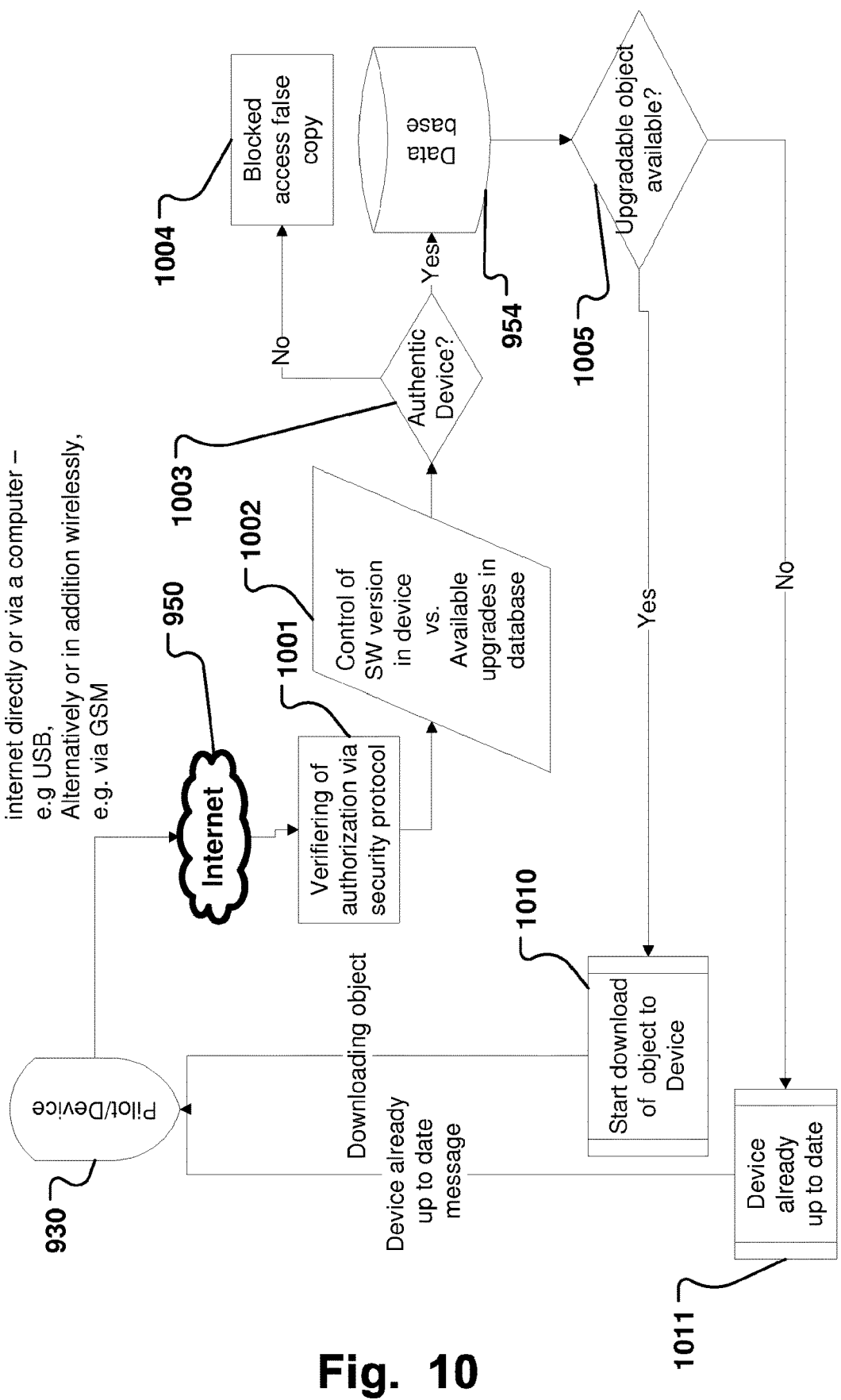
FIG. 10 is a schematic block diagram illustrating downloading of software (SW) and upgrading of SW to an apparatus as described with reference to FIGS. 1-8.

FIG. 10 is a schematic block diagram illustrating downloading of software (SW) and upgrading of SW to an apparatus as described with reference to FIGS. 1-8.

A device 930 is for this purpose connected to a database 954, e.g. via an Internet connection 950, or similar, as described above.

The database 954 may further provide functionality to the apparatus users (patients) to synchronize their apparatus/device 930 towards enabling download of new or changed flash memory (# 2) 23b information objects.

A verification 1001 of authorization is made via a security protocol, this to prevent unauthorized access to the database 954. Upon positive verification, a control 1002 of a SW version in device/apparatus 930 is made versus available SW upgrades in database 954. The latest available SW version in the database 954 is compared with the current apparatus/device SW version.

Authentic device/apparatus 930, checked in step 1003, are granted access to the database 954, or denied access depending if HW and SW identification clarifies the device/apparatus 930 as authentic, in order to prevent unauthorized copies of the device/apparatus 930 to get access to the upgrade database. In case of non verification, access is blocked at 1004, wherein connection to the database is blocked for the device/apparatus 930 that requested access due to authorization unconformity, i.e. the device/apparatus is regarded as unauthentic.

In case an upgradeable object is available is checked at step 1005. If the database 954 matches any available SW download objects with the version in the device/apparatus 930, a download of object to device/apparatus 930 is started at step 1010, whereupon identified upgrade objects are downloaded to the device/apparatus 930. If, on the other hand, the device/apparatus 930 already is up to date, no download objects are identified in step 1011. The device/apparatus 930 that is already up to date, and a corresponding message is displayed in the device/apparatus display.

Figure 11:
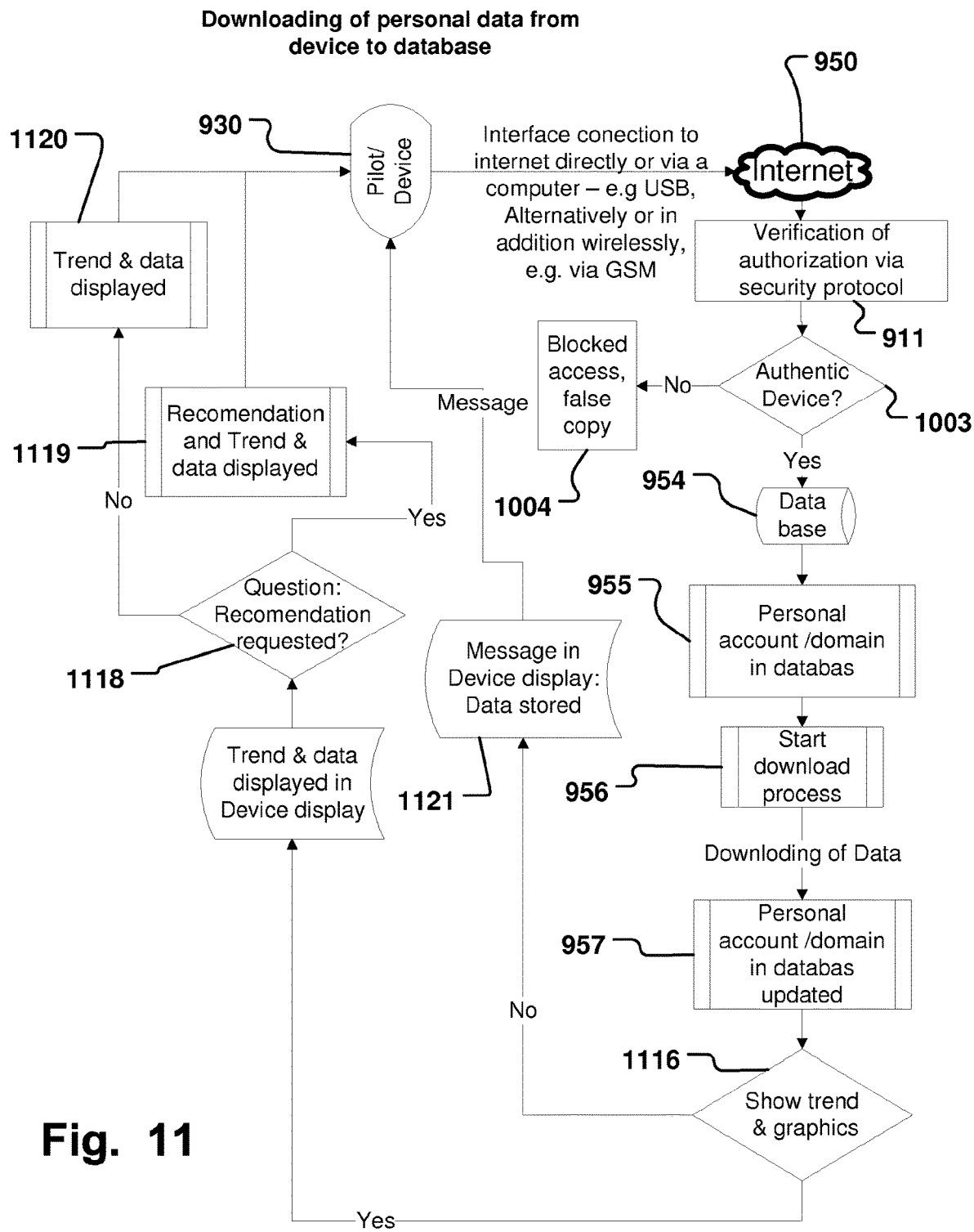
FIG. 11 is a schematic block diagram illustrating downloading of personal data from an apparatus as described with reference to FIGS. 1-8 to a database.

FIG. 11 is a schematic block diagram illustrating downloading of individual data for a person, e.g. the lifestyle data profile, from an apparatus as described with reference to FIGS. 1-8 to a database. The apparatus 930, is, as explained above connected to database 954 via a suitable connection, such as Internet 950, and performing steps 91, 1003, 1004, 955, 956, and 957.

In step 1116, a show trend & graphics decision may be made by the patient/user of apparatus 930 to visualize or not trends and graphics.

In step 1121 a message is displayed in the display of apparatus 930 that data is stored. Trends or graphics are not displayed.

In step 1117 the method proceeds to trend & data display in the display of apparatus 930, which is adapted for this task.

A question 1118 is presented to the user, if a recommendation is requested. This is a decision of the patient/user to visualize recommendations at this point in time or not. In step 1119 recommendation and trend data are displayed in the device/apparatus display. This type of recommendation is of general character and not a patient unique medical recommendation by an assigned health/medical professional, in contrast to the above described patient specific recommendation, perhaps based on a screening of data. In step 1120 trend & data are displayed. Thanks to this functionality, the patient/user may see the information objects that were transferred. This information objects are of cause available in the apparatus/device itself without connection to any database.

FIGS. 12 to 16 are schematic illustrations showing various practical implementations of an apparatus as described with reference to FIGS. 1-8.

Figure 12:
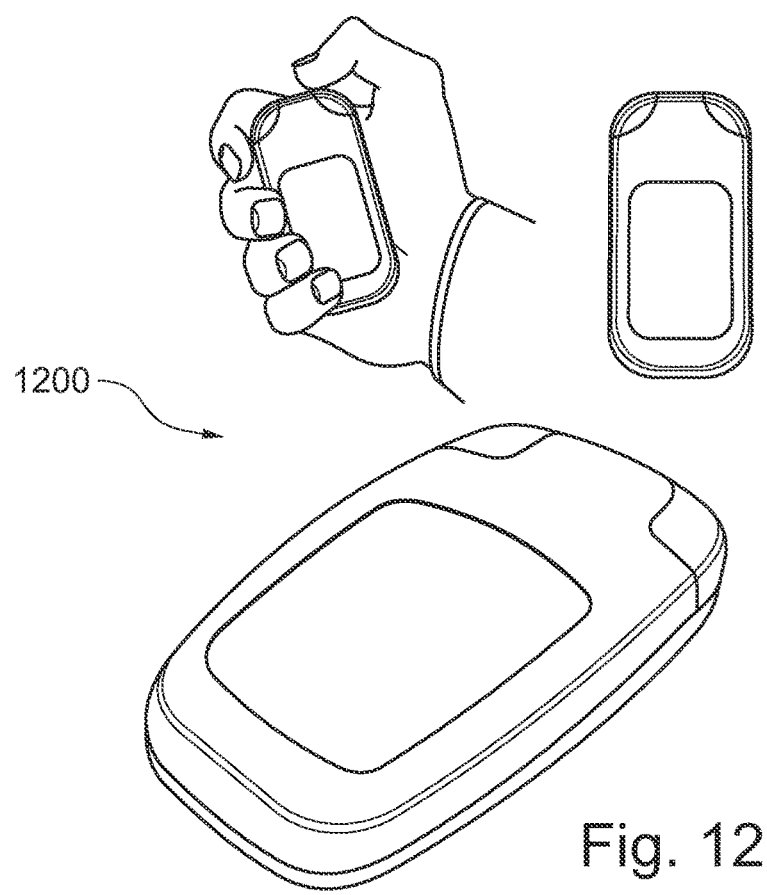
FIGS. 12 to 16 are schematic illustrations showing various practical implementations of an apparatus as described with reference to FIGS. 1-8

In FIG. 12, an implementation of apparatus 10 is illustrated in from of an apparatus 1200. This is a practical implementation example of a possible apparatus/device design as a small handheld portable unit in a classic soap like design.

Figure 13:
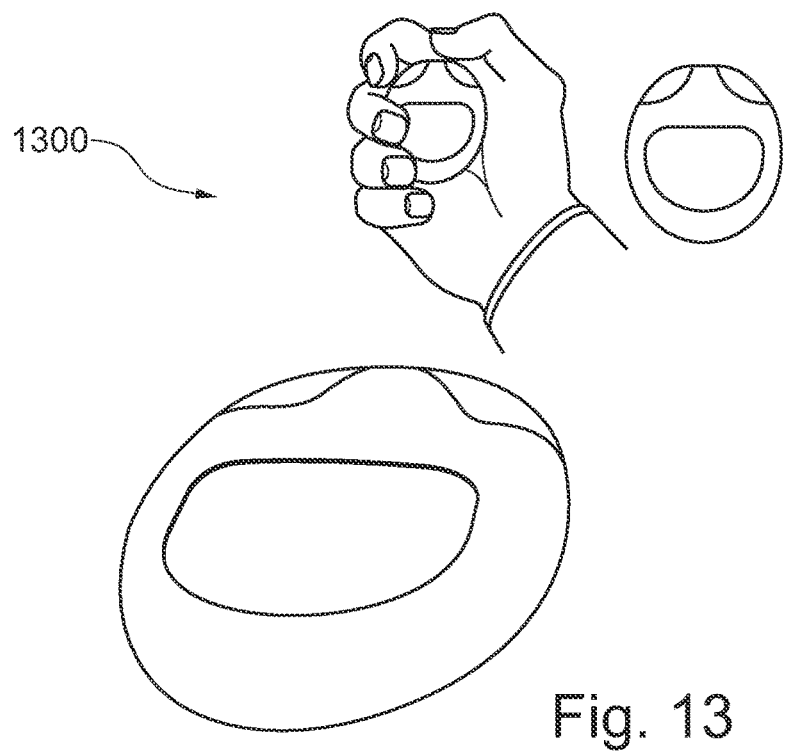

In FIG. 13, an implementation of apparatus 10 is illustrated in from of an apparatus 1300. This is a practical implementation example of a possible apparatus/device design as a small handheld portable unit in a round watch like design.

Figure 14:
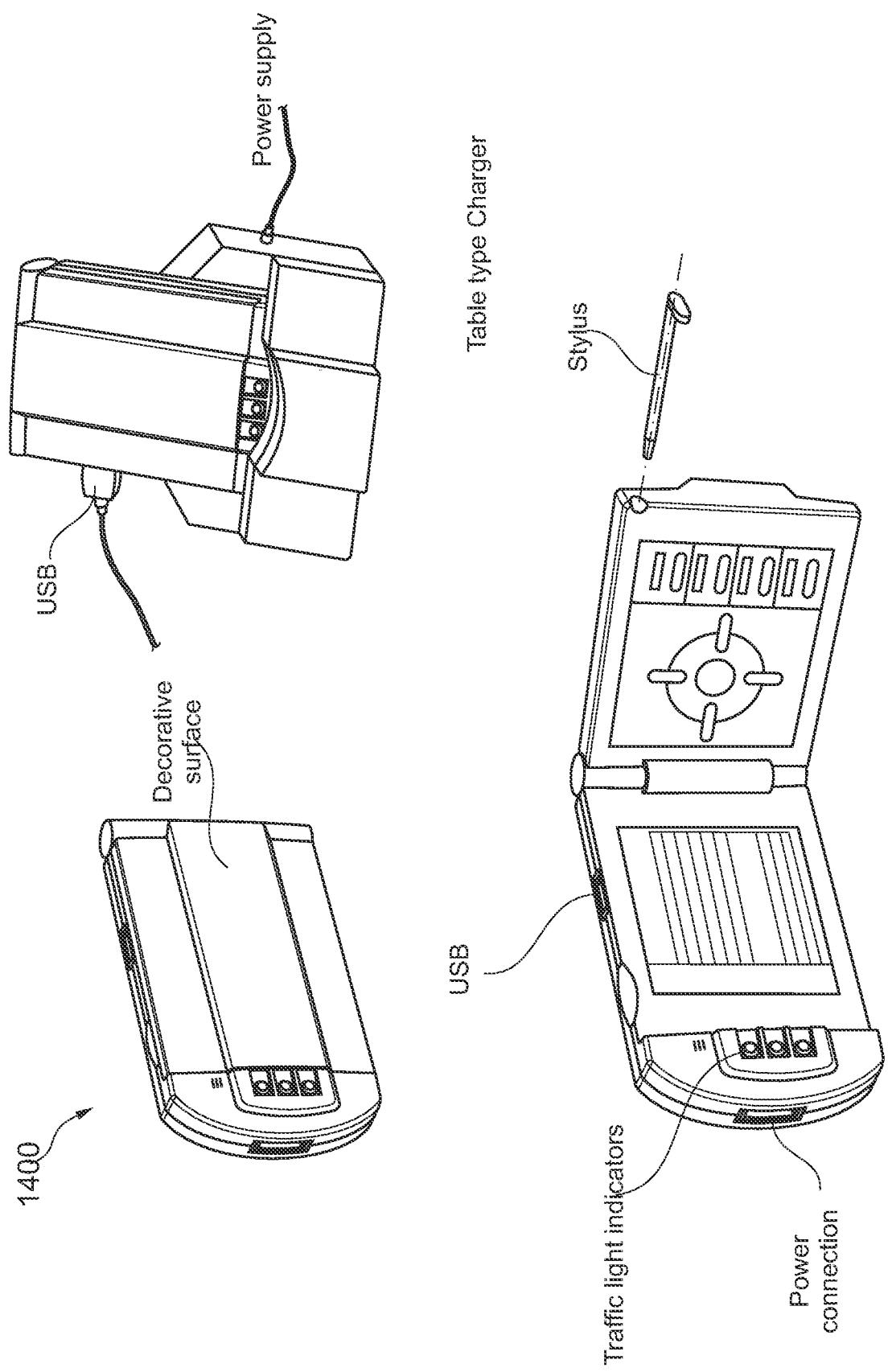

In FIG. 14, an implementation of apparatus 10 is illustrated in from of an apparatus 1400. This is a practical implementation example of a possible apparatus/device design as a handheld portable unit in a clam shell design.

Figure 15:
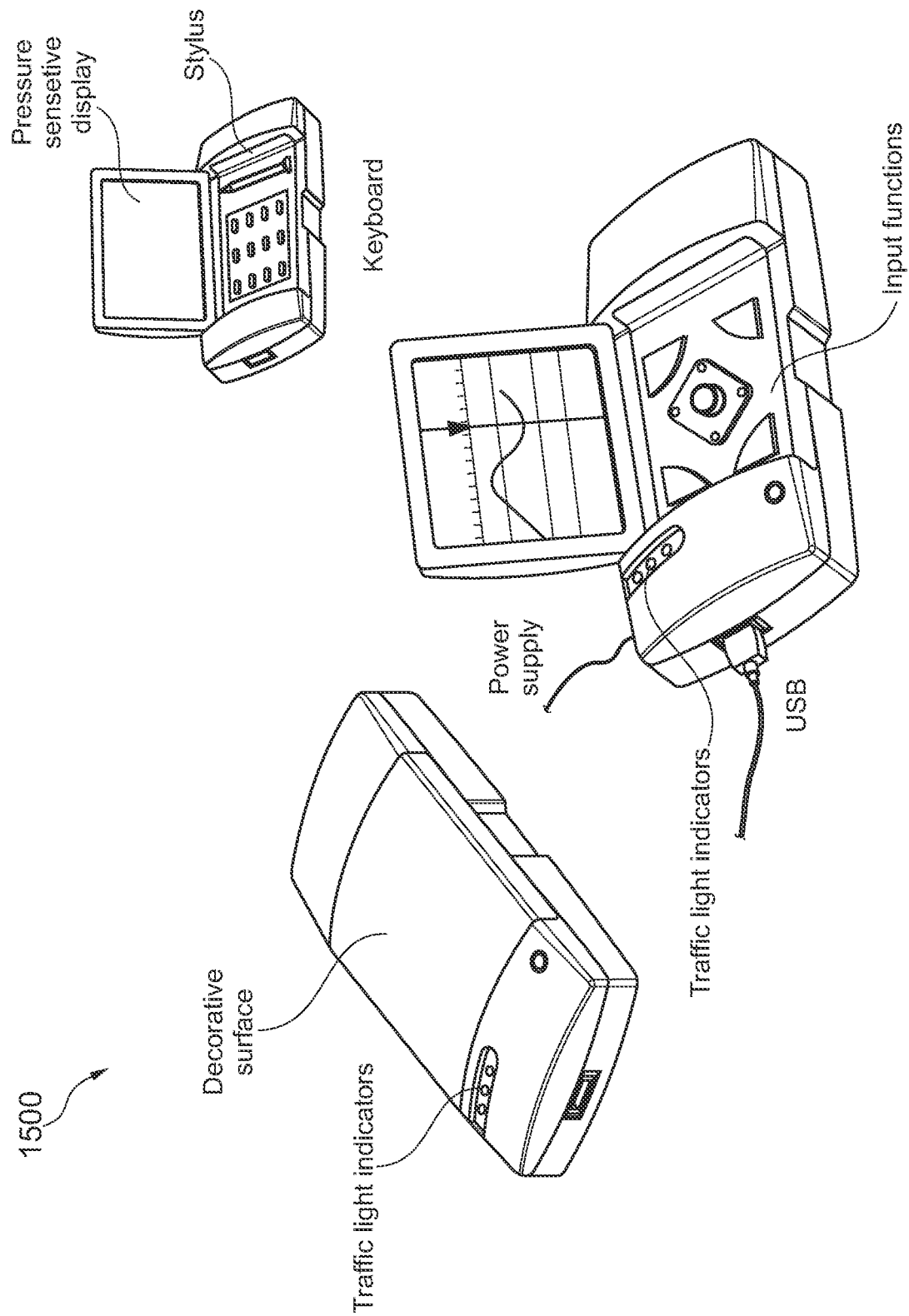

In FIG. 15, an implementation of apparatus 10 is illustrated in from of an apparatus 1500. This is a practical implementation example of a possible apparatus/device design as a handheld portable unit in a flip up front design.

Figure 16:
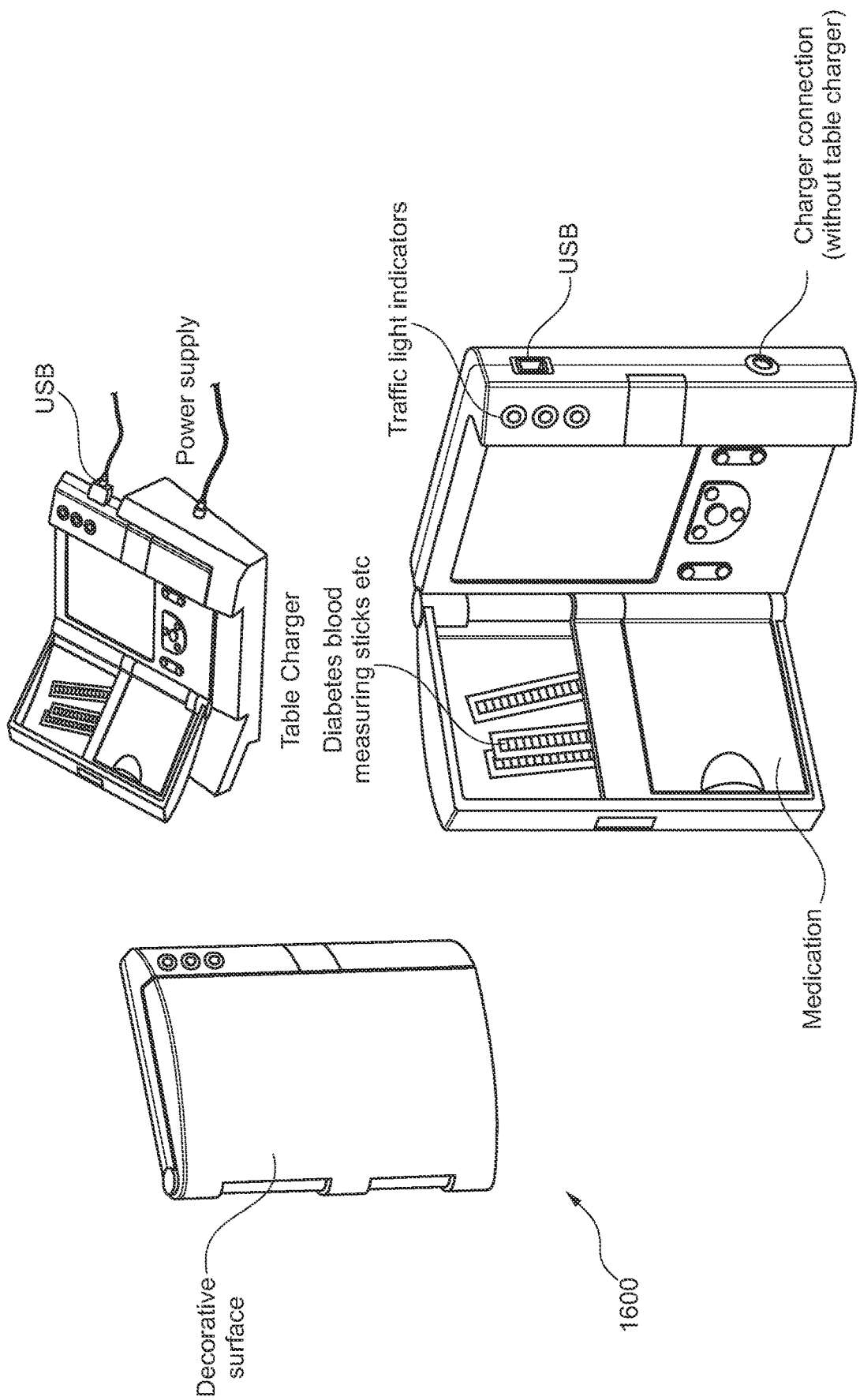

In FIG. 16, an implementation of apparatus 10 is illustrated in from of an apparatus 1600. This is a practical implementation example of a possible apparatus/device design as a handheld portable unit in a book like design with storage space for other diabetic accessories.

Figure 17:
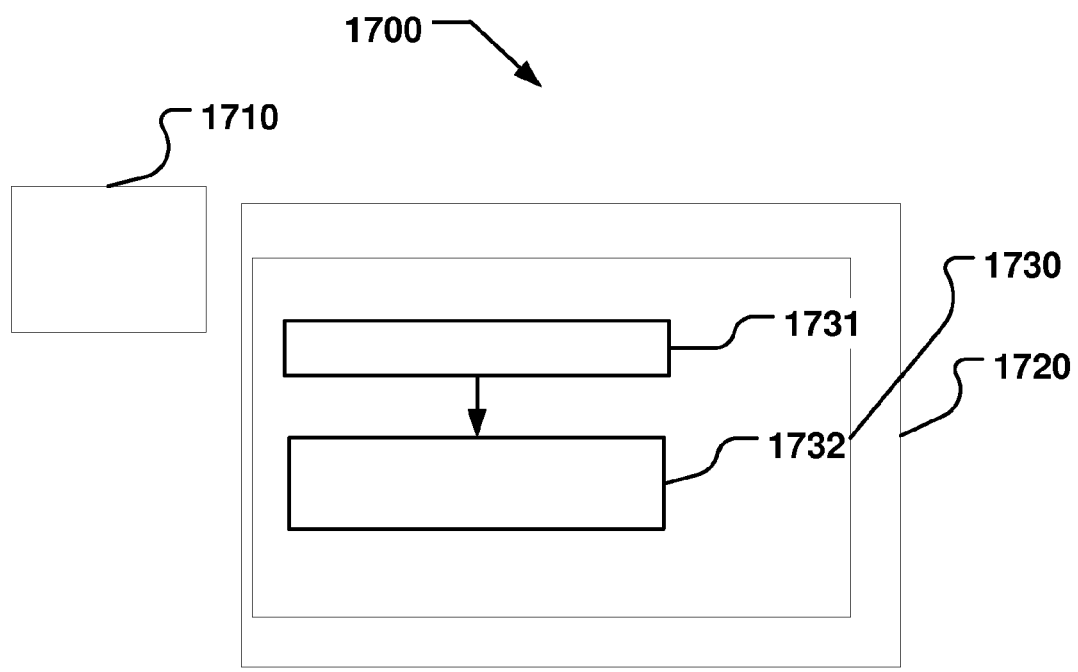
FIG. 17 is a schematic illustration of an embodiment of a computer program of an embodiment stored on a computer readable medium for execution by a processing unit.

FIG. 17 is a schematic illustration of an embodiment 1700 of a computer program 1730 stored on a computer readable medium 1720 for execution by a processing unit 1710, e.g. the specific first CPU 20 for processing patient critical applications or data objects. The computer program comprises a plurality of code segments 1731, 1732 for performing the above described methods.

FIGS. 18A-18F are flowcharts illustrating various menu principles of an apparatus as described with reference to FIGS. 1-8.

Figure 18A:
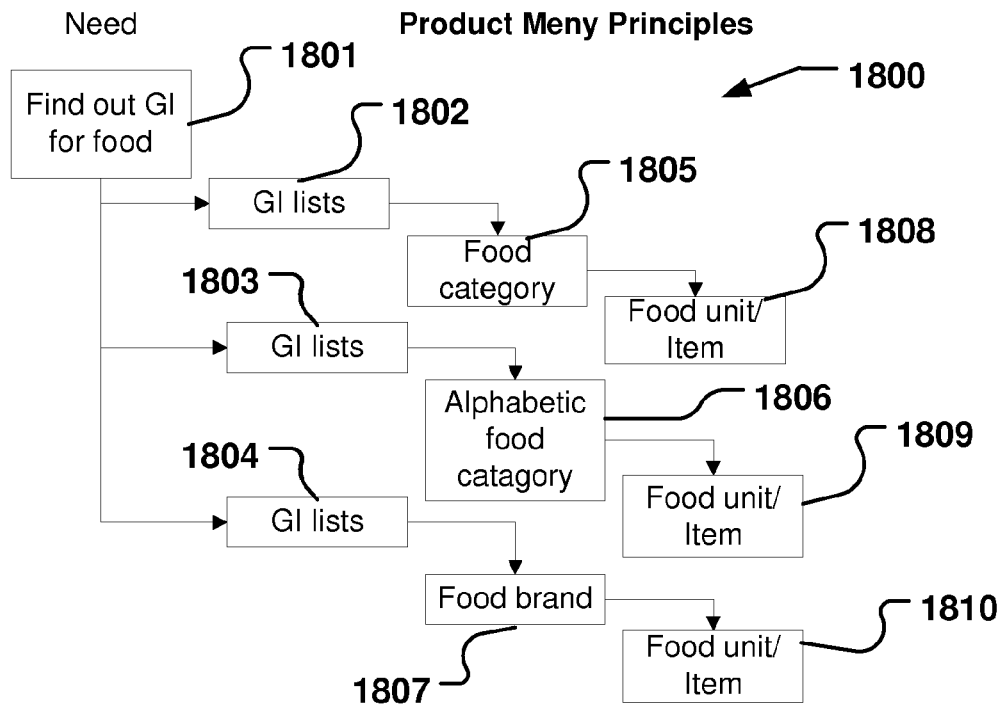
FIGS. 18A-18F are flowcharts illustrating various menu principles of an apparatus as described with reference to FIGS. 1-8.

FIG. 18A illustrates a menu structure 1800 for determining a GI value of a food product for entering database objects to create and/or adapt the lifestyle profile 361 data of apparatus 10. For this purpose, the user selects a button to determine the GI of a food that the user has eaten or intends to eat, at step 1801. The food may be chosen from various GI lists 1802, 1803, 1804, e.g. sorted by food category 1805, alphabetically 1806, or by food brand 1807. A food item is selected at one of steps 1808, 1809, 1810, respectively, and added to the lifestyle profile 361, from where the data object is available for subsequent utilization.

Figure 18B:
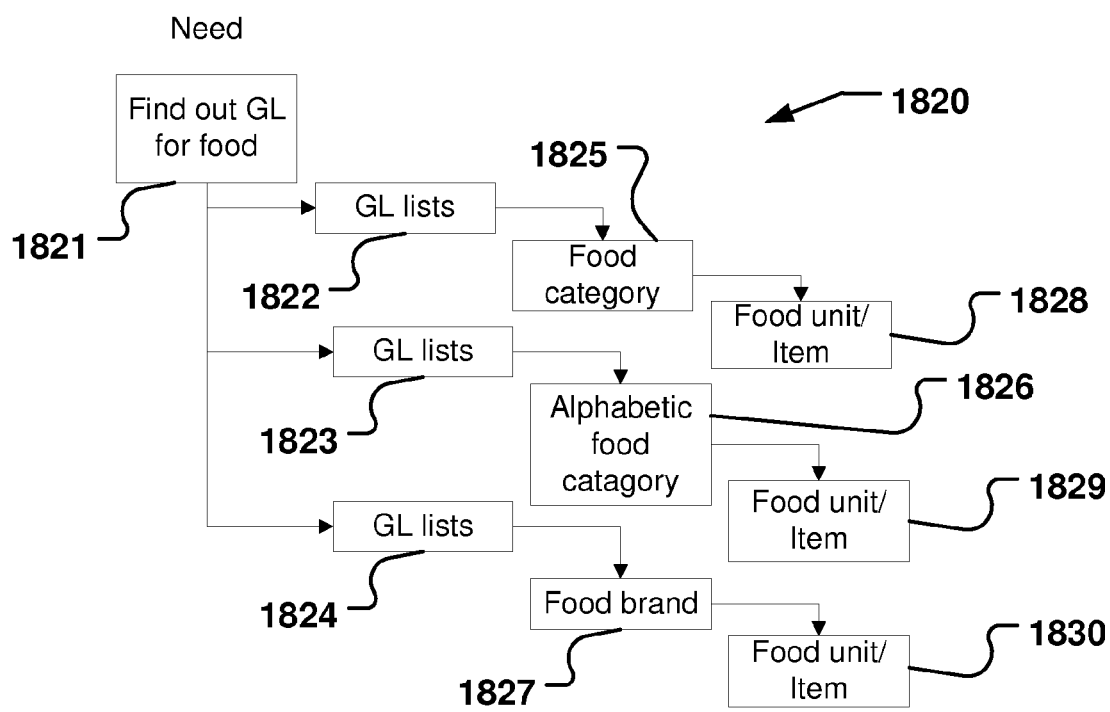

FIG. 18B illustrates a menu structure 1820 for determining a Glycemic Load GL value of a food product for entering database objects to create and/or adapt the lifestyle profile 361 data of apparatus 10. For this purpose, the user selects a button to determine the Glycemic Load GL of a food that the user has eaten or intends to eat, at step 1821. The food may be chosen from various Glycemic Load GL lists 1822, 1823, 1824, e.g. sorted by food category 1825, alphabetically 1826, or by food brand 1827. A food item is selected at one of steps 1828, 1829, 1830, respectively, and added to the lifestyle profile 361, from where the data object is available for subsequent utilization.

Figure 18C:
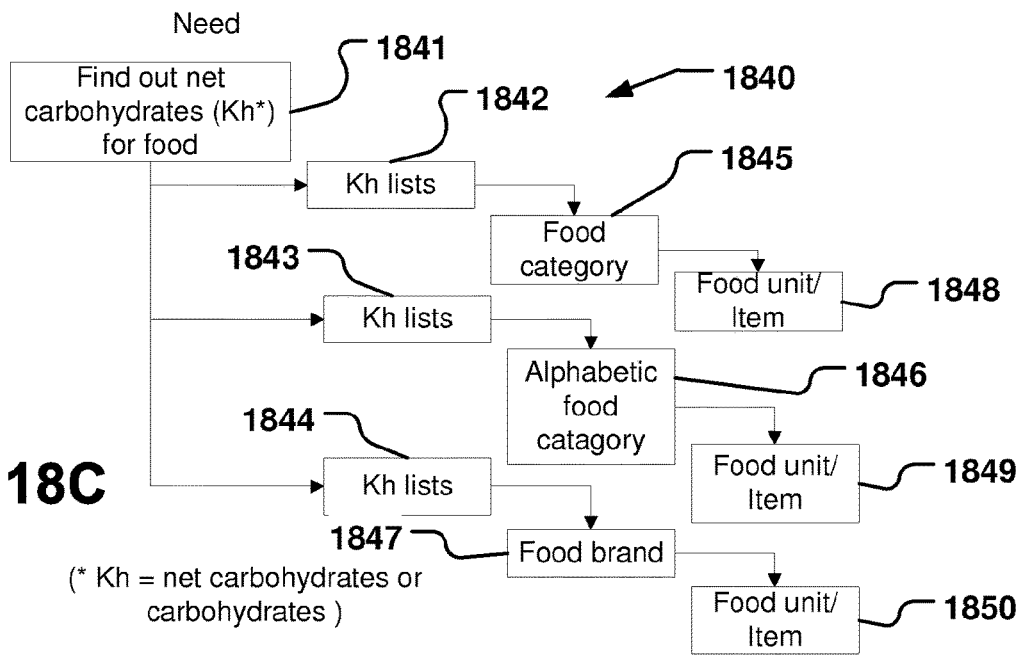

FIG. 18C illustrates a menu structure 1840 for determining a carbohydrate value of a food product for entering database objects to create and/or adapt the lifestyle profile 361 data of apparatus 10. For this purpose, the user selects a button to determine the carbohydrate contents of a food that the user has eaten or intends to eat, at step 1841. The food may be chosen from various carbohydrate lists 1842, 1843, 1844, e.g. sorted by food category 1845, alphabetically 1846, or by food brand 1847. A food item is selected at one of steps 1848, 1849, 1850, respectively, and then added to the lifestyle profile 361, from where the data object is available for subsequent utilization.

Figure 18D:
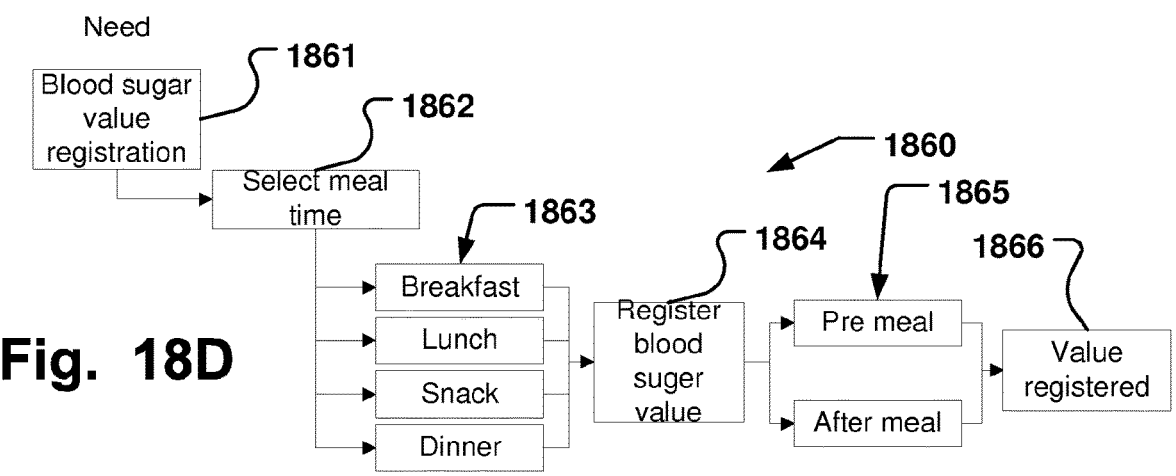

FIG. 18D illustrates a menu structure 1860 for entering 1861 a blood sugar value, e.g. measured by means of device 15. A meal time is selected at 1862, e.g. from a multiple choice list 1863 comprising breakfast, dinner, snack, lunch. The blood sugar value is entered in step 1864. In step 1865, the user may input if the blood sugar value was measured before or after a meal. A corresponding database object to the registered blood sugar value and time value is created in step 1866, which adapts the lifestyle profile 361 data of apparatus 10. The lifestyle profile 361 is thus updated and data objects are available for subsequent utilization.

Figure 18E:
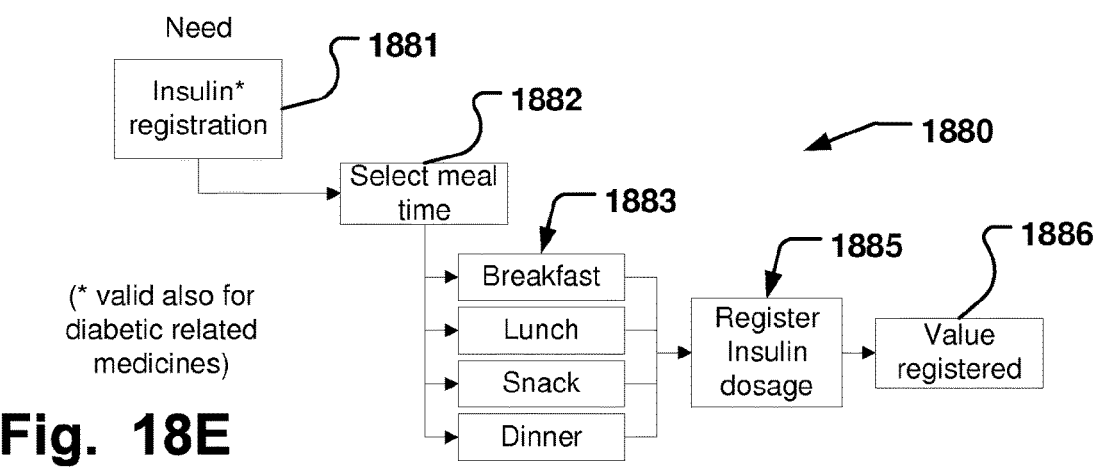

FIG. 18E illustrates a menu structure 1880 for entering 1881 a insulin intake value of the user. A meal time is selected at 1882, e.g. from a multiple choice list 1883 comprising breakfast, dinner, snack, lunch. The insulin value is entered in step 1884. A corresponding database object to the registered insulin value and time value is created in step 1886, which adapts the lifestyle profile 361 data of apparatus 10. The lifestyle profile 361 is thus updated and data objects are available for subsequent utilization.

Figure 18F:
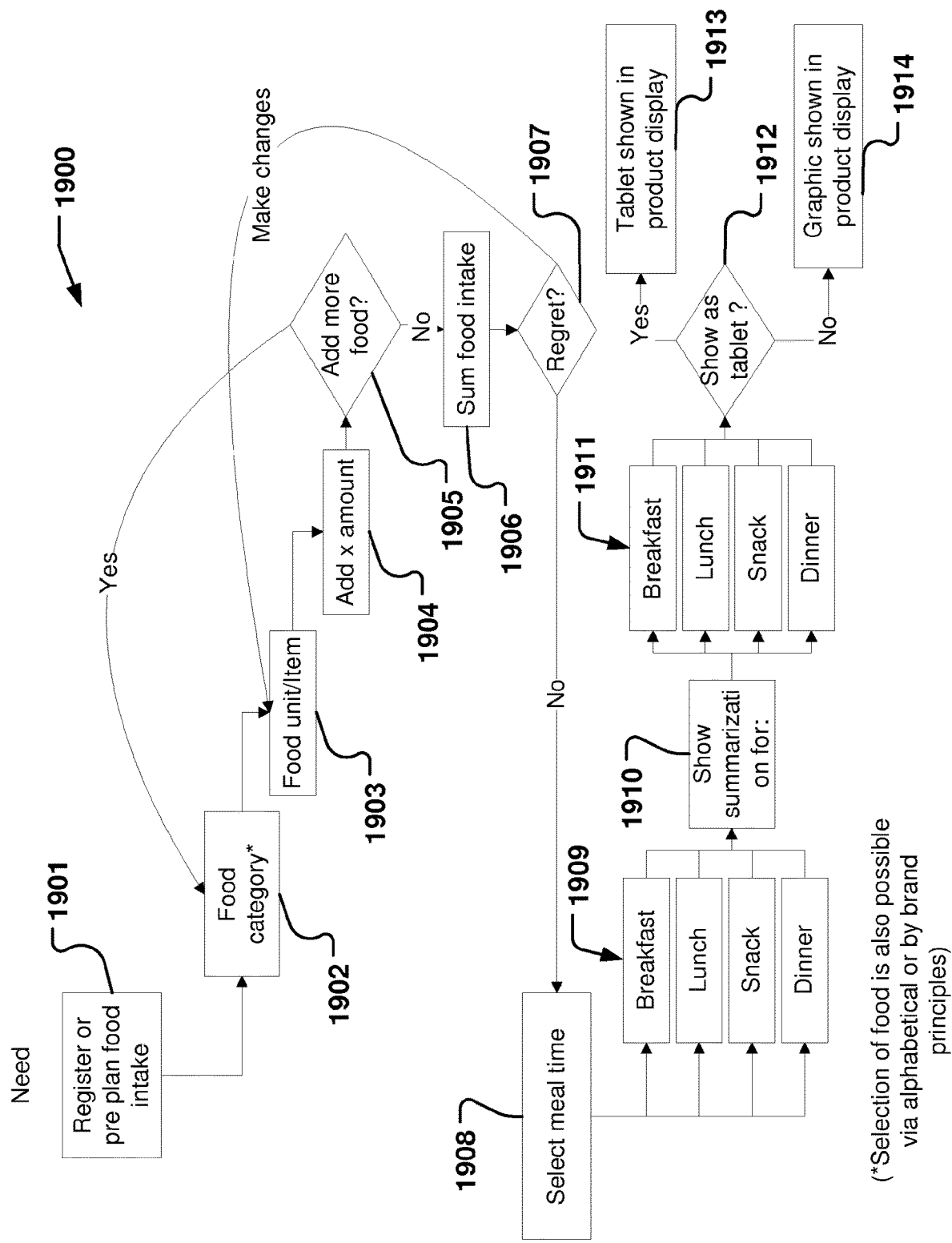

FIG. 18F illustrates a menu structure 1900 for registration or pre planning 1901 of food intake.

A food category is selected at 1902, the food unit/item is selected in step 1903 e.g. from an alphabetical, brand list or likewise. In step 1904 the amount of the food unit/item is entered in terms of quantified size, to add more food step 1905 is entered as needed. Summarization food intake for a specific selected item is calculated in step 1906; the user may make the choice to regret the selection in step 1907, depending on the result presented by step 1906. A Selection 1908 of mealtime is performed via multiple choice list 1909 comprising breakfast, lunch, snack and dinner.

Summarization mode for a selected food mealtime is entered at 1910 via a multiple choice list 1911 comprising breakfast, lunch, snack and dinner. The selected item is calculated and by selecting graphic visualization in step 1912, a tablet form may presented in the display 1913, or alternatively in graphical form in 1914. A corresponding database object to the registered values and time value is created, which adapts the lifestyle profile 361 data of apparatus 10. The lifestyle profile 361 is thus updated and data objects are available for subsequent utilization.

As will be appreciated by one of skill in the art, the present invention may be embodied as device, system, method or computer program product. Accordingly, the present invention may take the form of an entirely hardware embodiment, a software embodiment or an embodiment combining software and hardware aspects all generally referred to herein as a "circuit", "unit" or "module". Different units may also be implemented as an assembly or in a single unit as separate sub-units, e.g. two CPUs may be implemented in and integrated into a single circuit, such as an ASIC. Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

What is claimed is:

1. A mobile, portable apparatus adapted to be handheld and configured for predicting risks of various health conditions, comprising:
   at least one memory having stored thereon a plurality of food units and corresponding blood sugar affecting parameters for each food unit of said plurality of food units;
   wherein said at least one corresponding blood sugar affecting parameter is a stored value of one or more of the following parameters:
   glycemic indexes;
   glycemic loads; and,
   glycemic affecting parameters having a blood sugar lowering effect;
   that quantifies the effect the food unit will have on a blood sugar level;
   wherein said at least one memory is arranged and configured to communicate with a central processing unit;
   a blood sugar measuring device that takes bodily measurements from a user that are provided to the central processing unit;
   an input unit arranged and configured to allow the user to input a quantity of consumed food units selected from said plurality of food units;
   a display arranged and configured to display said at least one corresponding blood sugar affecting parameter as summed up blood sugar affecting parameters;
   wherein said central processing unit calculates said summed up blood sugar affecting parameters as calculated values concerning glycemic index totals or glycemic load totals based on the bodily measurements, the stored blood sugar values with respect to the glycemic indexes or the glycemic load, and the glycemic affecting parameters for said quantity of consumed food units;
   wherein said central processing unit is constructed and arranged for calculation of a lifestyle profile based on an interrelationship between said summed-up blood sugar affecting parameters.

2. The apparatus according to claim 1, wherein said central processing unit is arranged for calculation of net carbohydrates of each of said consumed food units, and wherein said display is adapted to display a total amount of said net carbohydrates.

3. The apparatus according to claim 1, wherein said apparatus comprises a timer unit for registration of a time of an event and for registration of time intervals between times of different events, and wherein said memory is adapted to store said total amount for providing a monitoring trend that extends over a certain time, retrospectively providing historical blood sugar affecting parameter information objects.

4. The apparatus according to claim 1, wherein said blood sugar affecting parameters comprise information objects about physical activities, health condition and medication of said user.

5. The apparatus according to claim 1, wherein said central processing unit is further adapted to process a measured blood sugar value of said user.

6. The apparatus according to claim 1, wherein said central processing unit is further adapted to process an insulin dosage and time of administration thereof to said user.

7. The apparatus according to claim 1, wherein said memory is adapted to store recommended values of blood sugar affecting parameters, and wherein said central processing unit is arranged to compare said calculated values with said recommended values for providing a compliance analysis.

8. The apparatus according to claim 1, wherein said memory is adapted to store information objects with regard to user's health condition, and wherein said central processing unit is arranged to compare said calculated values with said information objects with regard to user's health condition.

9. The apparatus according to claim 1, wherein said memory is arranged to be updated via connection to a remote database server via said communication unit.

10. The apparatus of claim 1 wherein said display further comprises:
    a blood sugar indicative curve in a variable time viewing scale;
    at least one indicator for a meal time relative said blood sugar indicative curve; and
    a range of normoglycemic blood sugar values in a band along said blood sugar indicative curve and adjacent bands of hyperglycemic and hypoglycemic ranges.

11. The apparatus according to claim 10, wherein said blood sugar indicative curve is an anticipated blood sugar curve based on said glycemic load.

12. The apparatus according to claim 11, wherein said blood sugar indicative curve is a glycemic index-based curve.

13. The apparatus according to claim 10, wherein said bands of normoglycemic, hyperglycemic and hypoglycemic ranges are color coded.

14. The apparatus according to claim 10, wherein, based on a pressure sensitive screen of said display, selected points or regions on said blood sugar indicative curve are selectable for providing further information or recommendations related to that point or region.

15. The apparatus according to claim 10, wherein a plurality of user selectable graphical buttons are provided for registration of meals or activities of a user.

16. The apparatus according to claim 10, comprising a status indicator.

17. The apparatus according to claim 10, comprising a historical status of a user of said apparatus at a selected point in time.

18. A system comprising:
 a plurality of apparatuses according to the apparatus of claim 1, each further comprising:
  a communication unit;
  a communication path from said communication unit to a remote database; and
 a computing device remote to said apparatuses configured to continuously screen data objects stored in said remote database in order to choose selected users from a population of users of said apparatuses, wherein said computing device is further configured to:
  select selected users from said population of users requiring recommendations from a health provider;
  identify noncomplying users from said selected users who are in non-compliance with said recommendations of said health provider based on whether a level of hypoglycemia or hyperglycemia meets or exceeds a threshold established by at least one of said noncomplying user's current blood sugar value, mean blood sugar value or historic blood sugar value, and deviations from said at least one of said noncomplying user's current blood sugar value, mean blood sugar value or historic blood sugar value level; and
  communicate with said noncomplying users via said communication unit.

19. The system according to claim 18, wherein said remote database is configured to allow users to download their lifestyle profiles data objects and for a health provider to follow up a patient population.

20. The system according to claim 18, wherein said communication path is useable by said health care provider to selectively communicate to said displays of the plurality of apparatuses.

21. The system according to claim 18, wherein said recommendations comprise a notice of medical follow up.

22. The system according to claim 18, wherein said computing device is further configured to: identify complying users from said selected users that are in compliance with said recommendations of said health provider, and provide a message of compliance with said recommendations to said complying users.

23. The system according to claim 18, wherein a multitude of said plurality of apparatuses are configured to synchronize data objects with said database.

24. The system according to claim 18, comprising a modality for communicating a lifestyle profile from at least one of said plurality of apparatuses directly to a physician.

25. The system according to claim 18, wherein said computing device is further configured to communicate a notice of follow up to said selected users via said communication unit.

26. The system according to claim 18, wherein said computing device is further configured to communicate unique recommendations to said selected users.

27. The system according to claim 18, wherein said computing device is further configured to electronically summarize blood sugar affecting factors, by:
 storing in a memory of each of said apparatuses a variety of data objects related to food units and glycemic indexes or glycemic loads thereof and a glycemic-affecting parameters having a blood sugar lowering effect for said food units,
 selecting specific food units of said stored variety of food units and entering an amount of respective food unit into said apparatus for further processing,
 processing said selected specific food units and amounts thereof in a central processing unit for providing at least one of glycemic index totals and glycemic load totals for said selected food units on the basis of the stored data objects.

28. The system according to claim 27 wherein said computing device is further configured to communicate with a user via a graphical user interface comprising:
 a blood sugar indicative curve in a variable time viewing scale;
 at least one indicator for a meal time relative said blood sugar indicative curve; and
 a range of normoglycemic blood sugar values in a band along said blood sugar indicative curve and adjacent bands of hyperglycemic and hypoglycemic ranges.

29. The system according to claim 18 wherein said computing device is further configured to:
 register a time of an event and for registration of time intervals between times of different events; and,
 store a total amount of said blood sugar affecting parameters for providing a monitoring trend that extends over a certain time, retrospectively providing historical blood sugar affecting parameter information objects.

30. The system according to claim 18 wherein said computing device is further configured to enter information objects of blood sugar affecting parameters comprising information objects about physical activities, health condition and medication of said user.

31. The system according to claim 18 wherein said computing device is further configured to enter information objects related to measured blood sugar value of said user.

32. The system according to claim 18 wherein said computing device is further configured to enter information objects related to an insulin dosage and time of administration thereof.

33. The system according to claim 18 wherein said computing device is further configured to compare summed up blood sugar values with recommended blood sugar values for providing a compliance analysis by said screening.

34. The system according to claim 18 wherein said computing device is further configured to compare summed up blood sugar values with information objects with regard to a user's health condition.

35. The system according to claim 18 wherein said computing device is further configured to communicate at least one of recipes, comprehensive step-by-step cooking instruction videos, and food shopping lists to selected users of said apparatuses.

36. The system according to claim 18, wherein said computing device is configured to identify users that are in non-compliance when no information is registered at all, or gaps exist in their lifestyle history registration track record.

37. A mobile, portable apparatus adapted to be handheld and configured for predicting risks of various health conditions, comprising:
 at least one memory having stored thereon a plurality of food units and blood sugar values for at least one related blood sugar affecting parameter for each food unit of said plurality of food units;

wherein said blood sugar values for at least one related blood sugar affecting parameter include one or more of:
glycemic indexes;
glycemic loads; and,
glycemic affecting parameters having a blood sugar lowering effect;
wherein said memory is arranged and configured to communicate with a central processing unit;
a blood sugar measuring device that takes bodily measurements from a user that are provided to the central processing unit;
an input unit arranged and configured to allow a user to input a quantity of said food units the user has consumed;
wherein said central processing unit calculates at least one of glycemic index totals and glycemic load totals based on the stored blood sugar values with respect to the glycemical indexes or the glycemical load, and the glycemic affecting parameters for said quantity of food units inputted by said user.

* * * * *